US012367948B2

(12) United States Patent
Spencer et al.

(10) Patent No.: US 12,367,948 B2
(45) Date of Patent: Jul. 22, 2025

(54) COMPUTER-IMPLEMENTED METHOD OF ANALYSING GENETIC DATA ABOUT AN ORGANISM

(71) Applicant: GENOMICS LIMITED, Oxford (GB)

(72) Inventors: Christopher Charles Alan Spencer, Oxford (GB); Gerard Anton Lunter, Oxford (GB); Peter James Donnelly, Oxford (GB); Vincent Yann Marie Plagnol, Oxford (GB)

(73) Assignee: GENOMICS LIMITED, Oxford (GB)

( * ) Notice: Subject to any disclaimer, the term of this patent is extended or adjusted under 35 U.S.C. 154(b) by 1132 days.

(21) Appl. No.: 15/733,547

(22) PCT Filed: Feb. 26, 2019

(86) PCT No.: PCT/GB2019/050525
§ 371 (c)(1),
(2) Date: Aug. 25, 2020

(87) PCT Pub. No.: WO2019/166792
PCT Pub. Date: Sep. 6, 2019

(65) Prior Publication Data
US 2020/0402614 A1 Dec. 24, 2020

(30) Foreign Application Priority Data

Feb. 27, 2018 (GB) .................................. 1803202.9

(51) Int. Cl.
| | |
|---|---|
| *G01N 33/48* | (2006.01) |
| *G06F 18/20* | (2023.01) |
| *G06N 3/00* | (2023.01) |
| *G16B 5/20* | (2019.01) |
| *G16B 20/40* | (2019.01) |
| *G16H 20/13* | (2018.01) |
| *G16H 70/40* | (2018.01) |

(52) U.S. Cl.
CPC ........... *G16B 20/40* (2019.02); *G06F 18/295* (2023.01); *G06N 3/002* (2013.01); *G16B 5/20* (2019.02); *G16H 20/13* (2018.01); *G16H 70/40* (2018.01); *C12Q 2600/112* (2013.01)

(58) Field of Classification Search
None
See application file for complete search history.

(56) References Cited

U.S. PATENT DOCUMENTS

2014/0032122 A1* 1/2014 Bader .................... G16B 20/00
702/19

FOREIGN PATENT DOCUMENTS

CN  107301330 A  10/2017

OTHER PUBLICATIONS

Aldous, Exchangeability and Related Topics, vol. 1117, Nov. 15, 2006, 98 pages.
Band et al., Imputation-Based Meta-Analysis of Severe Malaria in Three African Populations, PLOS Genetics, vol. 9, No. 5, May 2013, 13 pages.
Bellenguez et al., Genome-wide Association Study Identifies a Variant in HDAC9 Associated with Large Vessel Ischemic Stroke, Nature Genetics, vol. 44, No. 3, Mar. 2012, pp. 328-335.
Benner et al., Finemap: Efficient Variable Selection Using Summary Data from Genome-wide Association Studies, Bioinformatics, vol. 32, No. 10, 2016, pp. 1493-1501.
Chun et al., Limited Statistical Evidence for Shared Genetic Effects of eQTLs and Autoimmune-Disease-Associated Loci in Three Major Immune-Cell Types, Nature Genetics, vol. 49, No. 4, Apr. 2017, pp. 600-608.
Chung et al., GPA: A Statistical Approach to Prioritizing GWAS Results by Integrating Pleiotropy and Annotation, PLOS Genetics, vol. 10, No. 11, Nov. 2014, 14 pages.
Fearnhead, Exact and Efficient Bayesian Inference for Multiple Changepoint Problems, Statistics and Computing, vol. 16, 2006, pp. 203-213.
Giambartolomei et al., Bayesian Test for Colocalisation between Pairs of Genetic Association Studies Using Summary Statistics, PLOS Genetics, vol. 10. No. 5, May 2014, 15 pages.
Hackinger et al., Statistical Methods to Detect Pleiotropy in Human Complex Traits, Open Biology, vol. 7, No. 11, Nov. 1, 2017, 13 pages.
Han et al., A Method to Decipher Pleiotropy by Detecting Underlying Heterogeneity Driven by Hidden Subgroups Applied to Autoimmune and Neuropsychiatric Diseases, Nature Genetics, vol. 48, No. 7, Jul. 2016, pp. 803-812.
Hormozdiari et al., Colocalization of GWAS and eQTL Signals Detects Target Genes, The American Journal of Human Genetics, vol. 99, Dec. 1, 2016, pp. 1245-1260.
Kichaev et al., Integrating Functional Data to Prioritize Causal Variants in Statistical Fine-Mapping Studies, PLOS Genetics, vol. 10, No. 10, Oct. 2014, 16 pages.
Kwak et al., Gene- and Pathway-based Association Tests for Multiple Traits with Gwas Summary Statistics, Bioinformatics, vol. 33, No. 1, Jan. 2017, pp. 64-71.
Li et al., An Empirical Bayes Approach for Multiple Tissue eQTL Analysis, Biostatistics, vol. 19, No. 3, 2018, pp. 391-406.
Liu et al., Eps: An Empirical Bayes Approach to Integrating Pleiotropy and Tissue-specific Information for Prioritizing Risk Genes, Bioinformatics, vol. 32, No. 12, Feb. 15, 2016, pp. 1856-1864.
Mahmoud et al., TWIST1 Integrates Endothelial Responses to Flow in Vascular Dysfunction and Atherosclerosis, Circulation Research, Available online at: http://circres.ahajournals.org, Jul. 22, 2016, pp. 450-462.

(Continued)

*Primary Examiner* — Anna Skibinsky
(74) *Attorney, Agent, or Firm* — Kilpatrick Townsend & Stockton LLP

(57) ABSTRACT

Methods are disclosed for analysing genetic data about an organism. In one arrangement, input units are derived from studies that provide information about the association between genetic variants and phenotypes. Input units are assigned to one of a plurality of clusters, based on an assessment of the extent to which input units share genetic variants that affect any aspect of the phenotype corresponding to each input unit or any of the underlying biological mechanisms of the phenotype, thereby identifying phenotypes that share underlying biological mechanisms.

30 Claims, 11 Drawing Sheets

(56) References Cited

OTHER PUBLICATIONS

Maller et al., Bayesian Refinement of Association Signals for 14 Loci in 3 Common Diseases, Nature Genetics, vol. 44, No. 12, Dec. 2012, pp. 1294-1302.
Solovieff et al., Pleiotropy in Complex Traits: Challenges and Strategies, Nature Reviews Genetics, vol. 14, Jul. 2013, pp. 483-495.
Turley et al., Multi-trait Analysis of Genome-Wide Association Summary Statistics Using MTAG, Nature Genetics, vol. 50, Feb. 2018, pp. 229-237.
Wakefield, Bayes Factors for Genome-Wide Association Studies: Comparison with P-values, Genetic Epidemiology, vol. 33, 2009, pp. 79-86.
Wen et al., Integrating Molecular QTL Data into Genomewide Genetic Association Analysis: Probabilistic Assessment of Enrichment and Colocalization, PLOS Genetics, Available Online At: https://doi.org/10.1371/journal.pgen.1006646, Mar. 9, 2017, 25 pages.
Zhu et al., Bayesian Large-scale Multiple Regression with Summary Statistics from Genome-wide Association Studies, The Annals of Applied Statistics, vol. 11, No. 3, 2017, pp. 1561-1592.
Zhu et al., Integration of Summary Data from Gwas and eQTL Studies Predicts Complex Trait Gene Targets, Nature Genetics, vol. 48, Mar. 28, 2016, 9 pages.
Allen et al., Hundreds of Variants Clustered in Genomic Loci and Biological Pathways Affect Human Height, Nature, vol. 467, No. 7317, Sep. 29, 2010, pp. 832-838.
Farh et al., Genetic and Epigenetic Fine Mapping of Causal Autoimmune Disease Variants, Nature, vol. 518, No. 7539, XP055591899, Oct. 29, 2014, 21 pages.
Giambartolomei et al., A Bayesian Framework for Multiple Trait Colocalization From Summary Association Statistics, bioRxiv, Available Online At: URL: https://www.biorxiv.org/content/biorxiv/early/2018/02/13/155481.full.pdf, Feb. 13, 2018, 8 pages.
Li et al., A Probabilistic Framework to Dissect Functional Cell-type-specific Regulatory Elements and Risk Loci Underlying the Genetics of Complex Traits, bioRxiv, Available Online At: https://www.biorxiv.org/content/biorxiv/early/2017/10/24/059345.full.pdf, Jun. 16, 2016, 45 pages.
Nieuwboer et al., Gwis: Genome-wide Inferred Statistics for Functions of Multiple Phenotypes, American Journal of Human Genetics, vol. 99, No. 4, Oct. 6, 2016, pp. 917-927.
International Application No. PCT/GB2019/050525, International Search Report and Written Opinion, mailed on Jun. 6, 2019, 4 pages.
Pickrell et al., Detection and Interpretation of Shared Genetic Influences on 42 Human Traits, Nature Genetics, vol. 48, No. 7, XP055591430, Jul. 2016, 21 pages.
Saeed, Novel Linkage Disequilibrium Clustering Algorithm Identifies New Lupus Genes on Meta-analysis of Gwas Datasets, Immunogenetics, vol. 69, No. 5, XP036217074, Feb. 28, 2017, pp. 295-302.

\* cited by examiner

Fig. 5
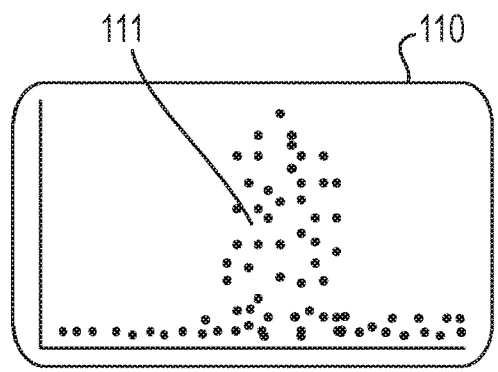
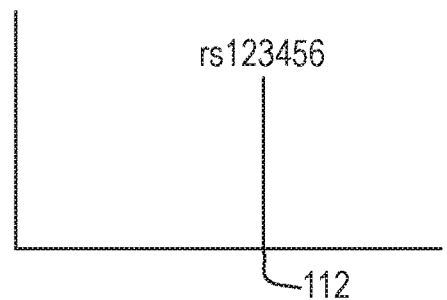
Fig. 6
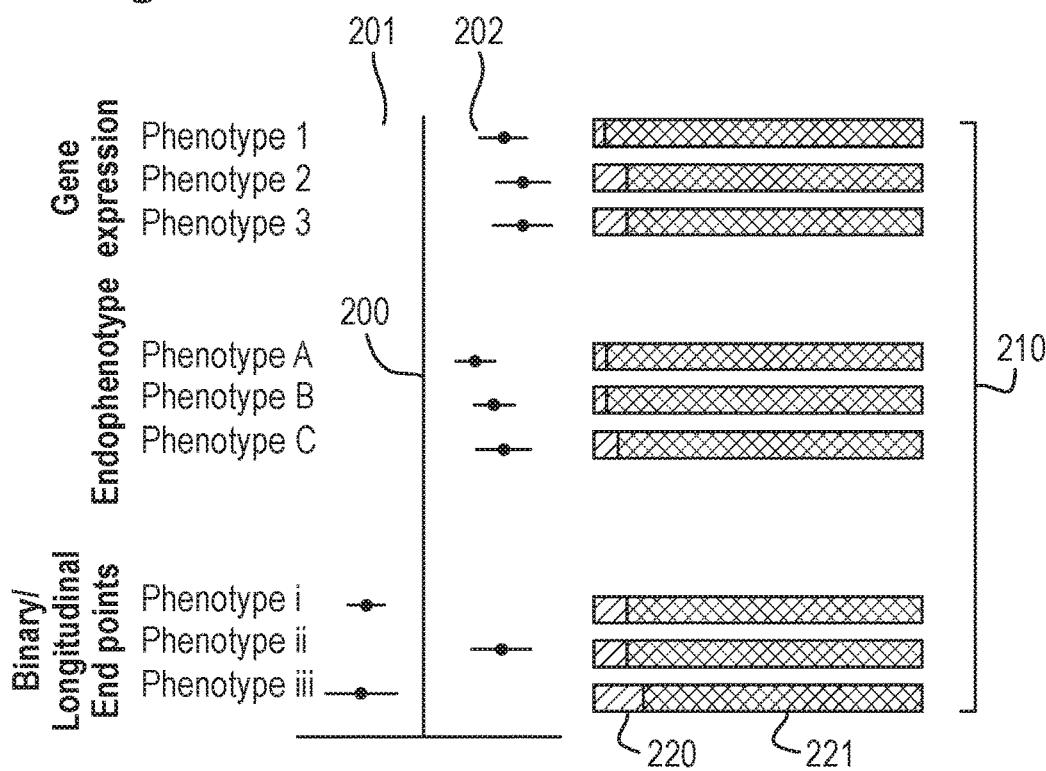

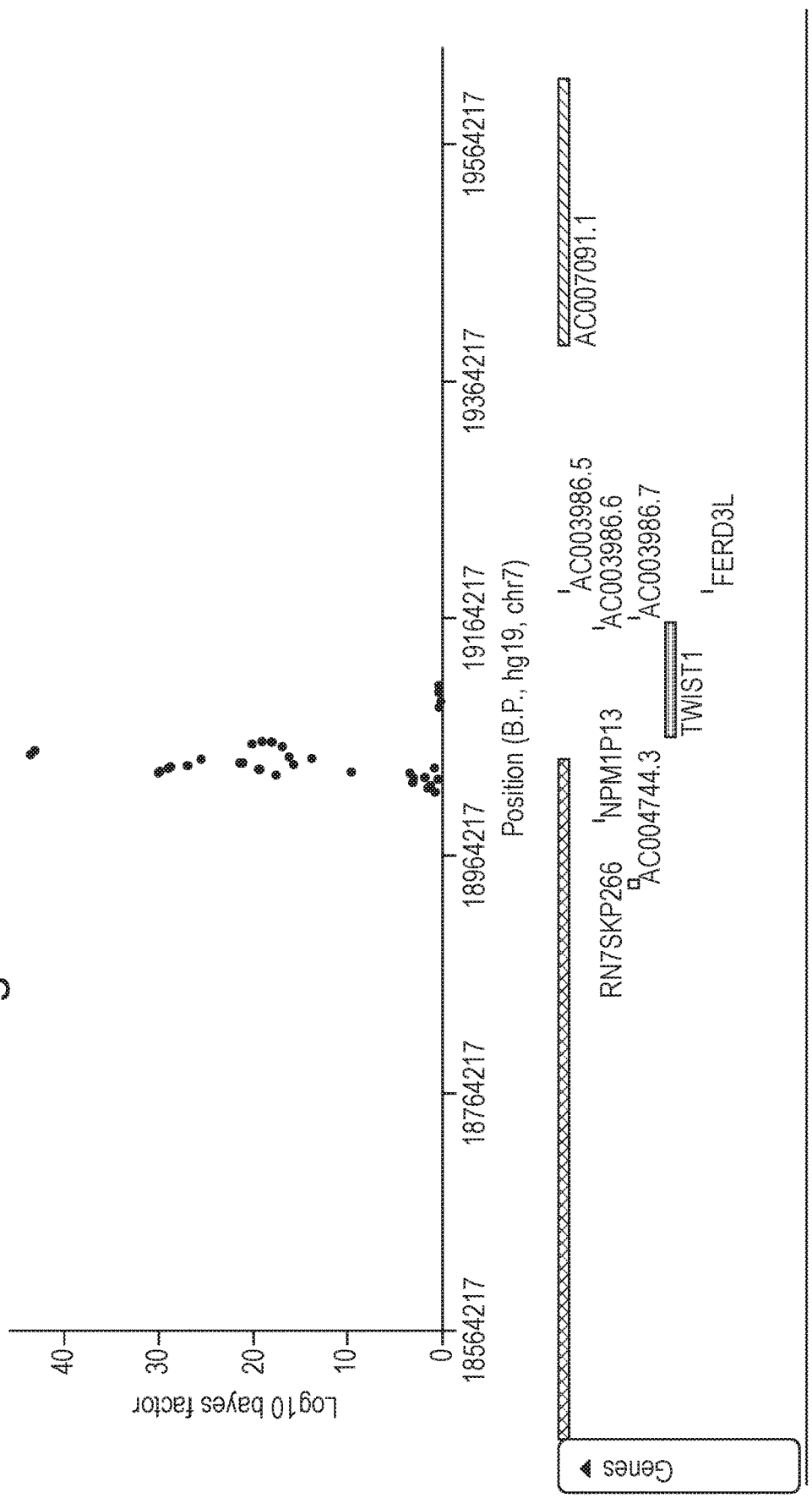

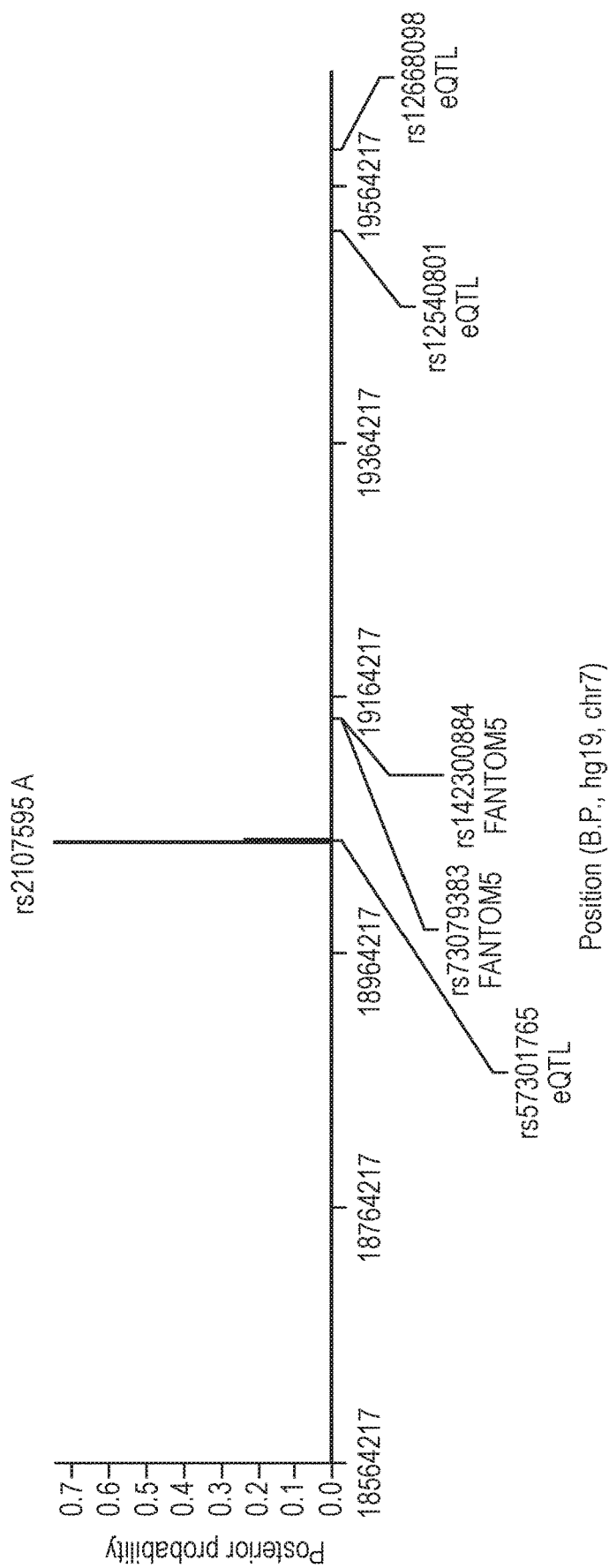

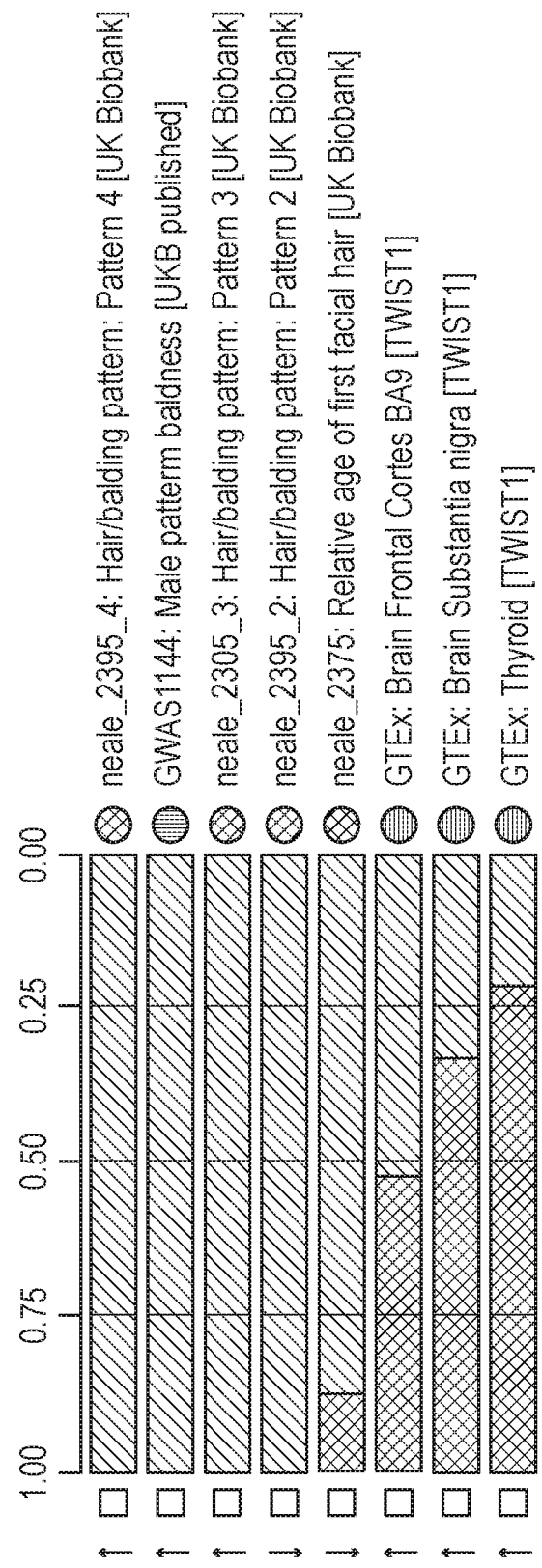

COMPUTER-IMPLEMENTED METHOD OF ANALYSING GENETIC DATA ABOUT AN ORGANISM

CROSS REFERENCE TO RELATED APPLICATIONS

This application is the National Stage of International Application No. PCT/GB2019/050525, filed Feb. 26, 2019, which claims priority to United Kingdom Application No. 1803202.9, filed Feb. 27, 2018, which are incorporated by reference herein in their entirety for all purposes.

The present invention relates to a method of analysing and interpreting large amounts of genetic and phenotype data about an organism in order to understand its biology.

Genetic association studies (GAS) assess the relationship between naturally-occurring genetic variation and a given phenotype. Since the mid 2000s, GAS (typically genome-wide association studies: GWAS, or association studies targeting single variants, or variants in a region of the genome, or GWAS restricted to a particular region of the genome), have been conducted on many thousands of (largely human) phenotypes, in millions of individuals, generating billions of potential links between genotypes and phenotypes. The resulting raw data is often then simplified to produce summary-statistic data. GAS summary statistic data consists of, for each genetic variant (whether imputed or observed), the inferred effect size ($\hat{\beta}$) of the genetic variant on the phenotype of the GAS and the standard error of the inferred effect size (SE). In what follows, we refer to a phenotype as being synonymous with a single study. However it is quite often the case that data are available from multiple different studies on the same or similar phenotypes, or from a single cohort from which multiple different phenotypes are measured.

Many different methods have been developed to use data from GAS to detect genetic variants that are associated with multiple phenotypes or traits (sometimes referred to as pleiotropy). Useful reviews in the field of human genetics are given by Solovieff et al. (2013)[1] and Hackinger & Zeggini (2017)[2]. Many existing 'single-point' methods analyse each genetic variant site separately. Examples of such single-point methods are provided in Table 1 of Hackinger & Zeggini (2017), and notably include GPA[3], MTAG[4] and EPS[5]. Other related methods focus on so-called 'expression quantitative trait loci' (eQTLs). An eQTL is a genetic variant that explains a fraction of the variance of a single gene expression phenotype. Notable eQTL-related methods include MT-eQTL[6], aSPU[7], and SMR[8]. Another related class of methods are single-point methods applied to raw GAS data (rather than GAS summary-statistic data). Examples of such single-point raw-data methods are provided in Table 2 of Hackinger & Zeggini (2017), and include BUHMBOX[9].

[1] Nat Rev Genet. 2013 July; 14(7):483-95
[2] Open Biol. 2017 November; 7(11). pii: 170125
[3] PLoS Genet. 2014 Nov. 13; 10(11):e1004787
[4] Nat Genet. 2018 February; 50(2):229-237
[5] Bioinformatics. 2016 Jun. 15; 32(12):1856-64
[6] Biostatistics. kxx048, https://doi.org/10.1093/biostatistics/kxx048 Preprint published online: 2017 Sep. 25
[7] Bioinformatics. 2017 Jan. 1; 33(1):64-71
[8] Nat Genet. 2016 May; 48(5):481-7
[9] Nature Genetics volume 48, pages 803-810 (2016)

While GAS offer valuable information about the relationships between genetic variation and phenotypes, there are considerable challenges in drawing robust causal links between genetic variants, genes, or biological pathways and one or more phenotypes. One difficulty is that genetic variants in a given region of the genome are often correlated with one another, a phenomenon referred to as linkage disequilibrium (LD). The occurrence of LD makes it difficult to distinguish a genetic variant with a causal effect ('causal variant') on a phenotype from other genetic variants correlated with it. Further difficulty arises when there are two or more causal genetic variants in the region of the genome being studied, and the association signals from these different causal genetic variants 'bleed over' to create apparent but spurious signals at other genetic variants (sometimes referred to as 'spurious pleiotropy'). These issues are particularly relevant when attempting to pool information across GAS of multiple phenotypes with the aim of maximising the statistical power to detect true effects. Whilst pooling together many (potentially hundreds or thousands of) GAS can improve the statistical power, this presents a significant challenge because pooling will only be statistically appropriate for phenotypes where it was known that they shared the same causal variant. In practice this information is typically not available—and certainly not available across large numbers of phenotypes—the consequence of which is that it is not clear which phenotypes to pool in a joint analysis. Even in situations where pooling might be based on prior information about the similarity of the phenotypes, the exact pattern of sharing of causal variants across phenotypes will vary across different regions of the genome. Making inference about these shared causal variants is critical for obtaining detailed and meaningful insights into the biology of an organism.

None of the single-point methods described above directly address the problem of identifying shared causal variants across phenotypes, or only do so in an ad-hoc way by proposing arbitrary rules of association and LD strength. These limitations can be overcome by moving to methods which use multiple variants across the same region of the genome to explicitly infer whether association signals in different phenotypes are potentially consistent with having the same causal variants (sometimes referred to as 'colocalisation').

To date, almost all colocalisation and related methods can only be applied to two GAS datasets at a time. Methods employing this pairwise approach include coloc[10], gwas-pw[11], eCAVIAR[12], enloc[13], and JLIM[14]. Inferring relationships between multiple phenotypes from such pairwise methods is problematic. The two main limitations are firstly, that the number of pairwise analyses increases quadratically with the number of GAS, and thus does not scale well if more GAS are added (data is already available on many thousands of GAS), and secondly, that the statistical power of such methods will be lost when attempting to detect signals that are shared by more than two phenotypes.

[10] PLoS Genet. 2014 May 15; 10(5):e1004383
[11] Nat Genet. 2016 July; 48(7):709-17
[12] Am J Hum Genet. 2016 Dec. 1; 99(6):1245-1260
[13] PLoS Genet. 2017 Mar. 9; 13(3):e1006646
[14] Nat Genet. 2017 April; 49(4):600-605

More recently, methods using GAS summary statistics data have been proposed that allow for the joint analysis of more than two phenotypes. A 2016 publication proposed the RiVIERA-MT[15] method, and another 2017 publication proposed mcoloc[16], a Bayesian framework similar to RiVIERA-MT. However, the authors of the 2017 publication note "the number of possible combinations increases exponentially as the number of traits increases, therefore computation time is a limiting factor and realistically it works well for up to four traits".

[15] doi: https://doi.org/10.1101/059345 Preprint published online 2016 Nov. 3; https://yueli-compbio.github.io/RiVIERA/
[16] doi: https://doi.org/10.1101/155481 Preprint published online 2017 Oct. 21

Given the existing prior art, there is still a need for a method which is capable of combining data from many GAS (for example more than 50, preferably more than 100, more preferably more than 500, more preferably more than 1000, more preferably more than 5000) to infer groups of phenotypes which share causal variants in a computationally efficient framework.

When applied to GAS data on different classes of phenotypes (covering a range extending from, gene expression, through endophenotypes, to binary and longitudinal endpoints) such a method would obtain a much more complete understanding of an organism's biology (by establishing links between variants and phenotypes, genes and phenotypes, and biological pathways and phenotypes). Efficient identification of groups of phenotypes sharing causal variants across the genome provides both specific insights into individual biological mechanisms (by establishing that a genetic variant perturbs biology in such a way as to have a causal impact on the group of phenotypes identified), and also allows for a comprehensive view of shared biological mechanisms (by analysis of patterns of phenotypic grouping across the genome). In the case of the application to human GAS data, such an in silico approach would permit insights into biological mechanisms which would otherwise have required direct, often invasive experimentation on human subjects.

It is an object of the invention to provide a computer-implemented method of analysing large amounts of genetic and phenotype data about an organism which is scalable without excessive increase in computational requirements.

According to an aspect of the invention, there is provided a computer-implemented method of analysing genetic data about an organism, comprising: receiving input data comprising a plurality of input units, wherein each input unit is derived from a study that provides information about the association between each of a plurality of genetic variants along the genome and a phenotype corresponding to the input unit; and then selecting a region or regions of the genome of an organism; and then for each of the selected regions, assigning each of the input units to one of a plurality of clusters, the assignment of the input units being based on an assessment of the extent to which input units share genetic variants within the selected region that affect any aspect of the phenotype corresponding to each input unit or any of the underlying biological mechanisms of the phenotype, thereby identifying phenotypes that share underlying biological mechanisms based on how the input units have been assigned to the clusters.

By analysing large numbers of phenotypes it can be shown that many causal genetic variants impact multiple phenotypes. Such findings permit an efficient representation of input data as a set of hidden clusters of phenotypes, which vary along the genome. Because each cluster is assumed to have a similar pattern of causal variation, the method establishes a biological connection between the phenotypes within the cluster. Thus, a method is provided which can use data from very many GAS (covering a range extending from, gene expression, through endophenotypes, to binary and longitudinal endpoints) simultaneously using reasonable computational resources in such a way as to provide detailed insights into biological mechanisms. By efficiently clustering many phenotypes the method may simultaneously provide improved ability to detect relationships between variants and phenotype, genes and phenotype, and/or biological pathways and phenotype, which in turn may provide further insights about genetic causality and detailed biological mechanisms of interest in an organism. The outputs of the method can be made more powerful still by corroborating findings with data from published biological research. In addition, the statistical power of embodiments of the present disclosure may allow detailed and reliable examination of real biological processes and determination of the effects of perturbing levels of molecules on cell and tissue function at little or no risk to individual organisms, and, in many instances, at high time- and cost-efficiency. This is possible because the input data—all of which will, in some embodiments, ultimately have been drawn from human research participants—is on a scale that is beyond the capability of other methods.

Since a single GAS typically examines a single phenotype, GAS may similarly be clustered, associated or assigned to a cluster, part of or members of a cluster with functionally equivalent meaning. In addition, input units derived from GAS may equivalently be clustered, associated or assigned to a cluster, part of or members of a cluster. In addition, we use the phrase causal variant to mean a genetic variant that affects the underlying biology of a phenotype under consideration. However we do not necessarily need to assume that the causal variant is in the input data; because of the presence of linkage disequilibrium nearby genetic variants can act as proxies for the causal variant when it is not included in the input data. In what follows we use "causal variant" to refer to the true causal variant when present in the input data, or to a proxy when it is not.

As shall be described in more detail below, the outputs of such a method can be utilised in various ways, in particular: (i) to generate a detailed understanding of biological mechanisms in an organism; (ii) in the discovery and development of therapeutics; (iii) calculation of an individual's chances of developing a particular disease, condition, or any other phenotype of interest; and (iv) to aid clinical decision making, by an individual or their healthcare professional, or both. Such applications of the method could make use of the inputs (typically the genetic information about an organism) and, more broadly, could leverage the outputs (i.e. detailed information about biological mechanisms).

In an embodiment, assigning each of the input units to one of a plurality of clusters further comprises using a prior distribution on the number and/or size of clusters.

This embodiment has the advantage that it enables computationally efficient approaches for inferring cluster membership, while not a priori constraining the number of clusters that is allowed. The method can therefore automatically adapt to the strength of evidence in the data. This built in adaptability permits the method to be applied to a variety of types and sizes of data without imposing strong assumptions about the genetic and biological relationship between phenotypes.

Imposing prior distributions which place less probability on a greater number of clusters has the benefit of preventing 'overfitting' (a modeling error which occurs when a function is too closely aligned to a limited set of data points). The improved detection of true clusters and protection against the detection of false clusters enhances the overall utility of the method for accurate interpretation of biological mechanisms.

In an embodiment, the plurality of clusters comprises a null cluster.

This embodiment has the advantage of explicitly including the possibility that data for a particular phenotype does not contain any causal variants. The approach benefits from the fact that the characteristics of the null cluster may be pre-determined and therefore do not need to be updated in light of information about other phenotypes in the null cluster, leading to computational efficiency at scale. The identification of phenotypes with evidence against the presence of a causal variant (i.e. by way of strong assignment to the null cluster) is important for defining the biological relationship between phenotypes. Evidence of absence of effect of a causal variant is central to many downstream applications of the output (for example that the effect of modulating a gene or pathway does not affect a specific phenotype).

In an embodiment, the assignment of each of the input units to one of a plurality of clusters is based on assessing said assignment using a probabilistic model.

This embodiment implements the clustering within a probabilistic model which describes the joint distribution of the data and the unobserved parameters of interest which include labels of cluster membership. The approach benefits from being able to characterise the certainty around cluster assignment. In addition, the space of possible cluster assignments may be explored through a Markov chain Monte Carlo algorithm. Such a probabilistic model has widespread application in decision making processes made on the basis of the outputs of the method.

In an embodiment, the method computes a measure of similarity between each input unit and each cluster. This measure of similarity can be used directly to marginalise out over uncertainty in cluster assignment in performing inference, particularly on the underlying causal variants, or can be used to characterise the output of the algorithm. This measure of similarity can be calculated in several ways. In one embodiment, the assignment of input units to one of a plurality of clusters is performed repeatedly, resulting in a plurality of configurations that together reflect the inherent uncertainty of assignments of input units to clusters that results among other factors from the limited amount of available input data. After performing said assignments repeatedly for a pre-set number of times or until a pre-specified condition is met, said measure of similarity is computed as the actual frequency that each input unit has been a member of each cluster during the said process. In another embodiment said measure of similarity is computed as the probability of assigning an input unit to a cluster by the process used to assign input units to clusters in the first place. Indeed the probability of the assignment of input units to one of a plurality of clusters is calculated in order to sample the cluster assignments.

In an embodiment, the method further comprises, for each of one or more of the plurality of clusters, using the set of characteristics of the cluster to identify one or more lead genetic variants from the plurality of genetic variants that are likely to be causal for one or more phenotypes corresponding to the cluster. This embodiment adds biological interpretation and increases the statistical power to identify clusters by using all of the phenotypes within a cluster to characterise the set of genetic variants that are likely to be causal for one or more phenotypes corresponding to the cluster. Existing methods attempt to explicitly identify a causal variant from evidence of significant association with a given single phenotype. This embodiment can treat such information as a "nuisance variable" and integrate it out analytically for the purposes of efficiently identifying clusters, whilst maintaining the ability to use the output of the algorithm to infer causal variants. The utility of this approach is to further enhance the ability to link the phenotypes within a cluster to the function of the genome, and often to aid in the identification of genes, therefore providing further insight into the biological mechanisms perturbed by the causal variant.

In an embodiment, the method further comprises identifying a group of phenotypes corresponding to input units which are assigned to the same cluster across the plurality of sets with a frequency above a predetermined frequency threshold.

This approach has the advantage of being able to more easily identify molecular mechanisms which underlie a phenotype of interest. For example, it is possible to identify all the phenotypes that are either enriched or depleted in clusters that are associated with a phenotype of interest. This information allows a detailed exploration about the shared or distinct genetic bases to the phenotypes under analysis.

In this embodiment the clusters may be used to identify a set of causal variants within a region, each causal variant possibly corresponding to more than one cluster or all clusters within the region, and each cluster possibly corresponding to more than one causal variant within the region, from which a joint estimate of the effect of the set of causal variants on each of the studies can be obtained adjusting for the correlation in the estimated effects as necessary. These joint estimates provide further biological information about the relationship between the phenotypes under study in the generation of the input units. Similarities between clusters can then be determined by directly comparing the effect size estimates across studies and between clusters.

Furthermore, in an embodiment that has the further characteristic of allowing the possibility that more than one causal (or lead) genetic variants are identified for each cluster, comparison of the phenotypes between clusters may occur on the basis of an assessment of shared cluster membership or by an assessment of the consistency of the effect sizes at the identified causal variants across input units, in each case across a plurality of sets of clusters.

An embodiment further comprises taking account of correlations or other known relationships between studies which provide information used to derive input units.

This embodiment has the advantage of being able to take account of pre-existing information or knowledge about biological mechanisms in the organism to improve the accuracy and reliability of the results. This information may include information about the likelihood of specific variants being causal in general or for specific phenotypes, or information about the likelihood of phenotypes having shared cluster membership. This information may further include information obtained by the method beyond the region of interest, including information obtained from genome-wide data, which then enables the method to learn and benefit from correlations between studies or input units.

An embodiment further comprises performing the method for each of a plurality of selected regions of the genome, thereby providing a plurality of sets of clusters containing assigned input units, each set of clusters corresponding to a different one of the selected regions, and associating a first subset of one or more clusters from a first set with a second subset of one or more clusters from each of one or more other sets by assessing a similarity between phenotypes corresponding to input units in the first subset of clusters with phenotypes corresponding to input units in the one or more second subsets of clusters.

This embodiment has the advantage that the sets of clusters identified can be further analysed to provide insights into shared biological mechanisms. A deterministic or probabilistic approach to clustering the clusters establishes a relationship between different biological perturbations in terms of their impact on an organism's phenotypes, therein providing insights into linked biological mechanisms and processes. For example, a subset of clusters that shows associations with a disease of interest across a number of genomic regions can be further interrogated to look for both shared and distinct pathogenic mechanisms.

Embodiments of the invention will be further described by way of example with reference to the accompanying drawings.

FIG. 5 shows a cluster with an associated lead variant.

FIG. 6 shows an output of an embodiment of the method.

Figure 1:
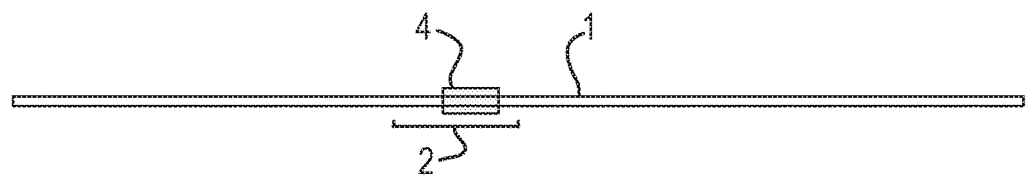
FIG. 1 shows a gene and region within a genome.

The present method aims to cluster phenotypes and allow an interpretation of those clusters in terms of shared biological mechanisms. Phenotypes may be said to be clustered, associated or assigned to a cluster, or part of or a member of a cluster with equivalent meaning.

Examples of phenotypes that are the subject of GAS include: a level of expression, and regulation of expression, of a gene (and related nucleotide sequences); epigenetic characteristics (for example, nucleotide modification, chromosomal conformation); a level of abundance of a protein or peptide; the function and/or molecular structure of a protein or peptide; a quantity of a molecule in the organism (for example a drug, a hormone, a DNA molecule, or an RNA molecule, a metabolite, a vitamin); characteristics of biochemical and metabolic processes (for example basal metabolic rate, prothrombin time, activated partial thromboplastin time); cellular morphology and function (for example, red blood cell mean corpuscular volume, absolute neutrophil count); tissue morphology and function (for example, bone mineral density, hair colour); organ and organ system morphology and function (for example, left ventricular ejection fraction, forced vital capacity); any response to an external stimulus or stimuli (for example light, sound, touch or any other sensory input); any response to exposure to a substance or pathogen (for example dietary input, drugs, gases, viruses, bacteria); behavioural and lifestyle characteristics (for example, smoking, alcohol consumption, occupation); reproductive and life course characteristics and function (for example age at menarche, placental weight, number of years in education); the onset, trajectory, and prognosis of a disease or condition (for example diabetes, cardiovascular disease, obesity); a measurable anatomical characteristic (for example, body-mass index, lean muscle mass, body fat percentage); a measurable physiological or functional characteristic (for example, heart rate, blood pressure, intelligence); and measurable psychological or cognitive characteristics (for example, metrics of fluid intelligence, psychotic symptoms). Any of these measurements might be absolute or relative.

One embodiment of the disclosure uses a form of model-based clustering, which can be directly interpreted as identifying shared causal genetic variants within clusters. Other approaches to the clustering of large sets of data, based on distance metrics or scalable pattern recognition methodology could also be applied in this context.

At its highest level, the disclosure provides computer-implemented methods of analysing genetic data about an organism, where input units are derived from studies that provide information about the association between genetic variants and phenotypes. Input units are then assigned to one of a plurality of clusters, based on an assessment of the extent to which input units share genetic variants that affect any aspect of the phenotype corresponding to each input unit or any of the underlying biological mechanisms of the phenotype, thereby identifying phenotypes that share underlying biological mechanisms. The assessment may be based on an assessment of the similarity between measures of association or the pattern of such measures, at some or all of the plurality of genetic variants.

An example embodiment will now be described which uses particular implementations of various aspects of the method. The example embodiment comprises a method using GAS data to identify combinations of: (i) a set of clusters to which phenotypes (and the GAS of which the phenotype is the subject) are assigned; and (ii) for each cluster, at least one lead (i.e. presumed causal) genetic variant in a selected region. The example embodiment comprises a probabilistic model (more specifically a Bayesian statistical model) that describes the joint distribution of the input units and the latent variables of the model, which includes clustering assignments. The embodiment uses a Markov chain Monte Carlo algorithm to explore the posterior distribution of this model, and therefore the space of possible cluster assignments. The Markov chain Monte Carlo algorithm produces a sample from this posterior distribution, and this sample is used to produce the final clustering. In doing so, the embodiment achieves the goal of identifying clusters of phenotypes and associated genetic variants that share underlying biological mechanisms.

In the example embodiment, the method has six main parts: namely: (i) a method to identify selected regions of the genome to analyse; (ii) a method to specify a prior distribution over the number and/or size of phenotype clusters that exist in the selected region; (iii) a method to calculate a likelihood function evaluating the probability that a particular genetic variant or genetic variants are causal for a given GAS/phenotype; (iv) a method to perform a meta analysis that combines these likelihoods across studies; (v) a method of assigning the GAS to clusters; and (vi) a system to run step (v) iteratively until some convergence criterion is met, and use the series of assignments at each iteration to obtain final cluster assignments. Of these steps, (ii)-(v) can be considered as the specification of the probabilistic model. In the example embodiment, which uses a Bayesian model, these steps are designed to sample from the posterior distribution of that model via a Markov Chain Monte Carlo algorithm.

Figure 2:
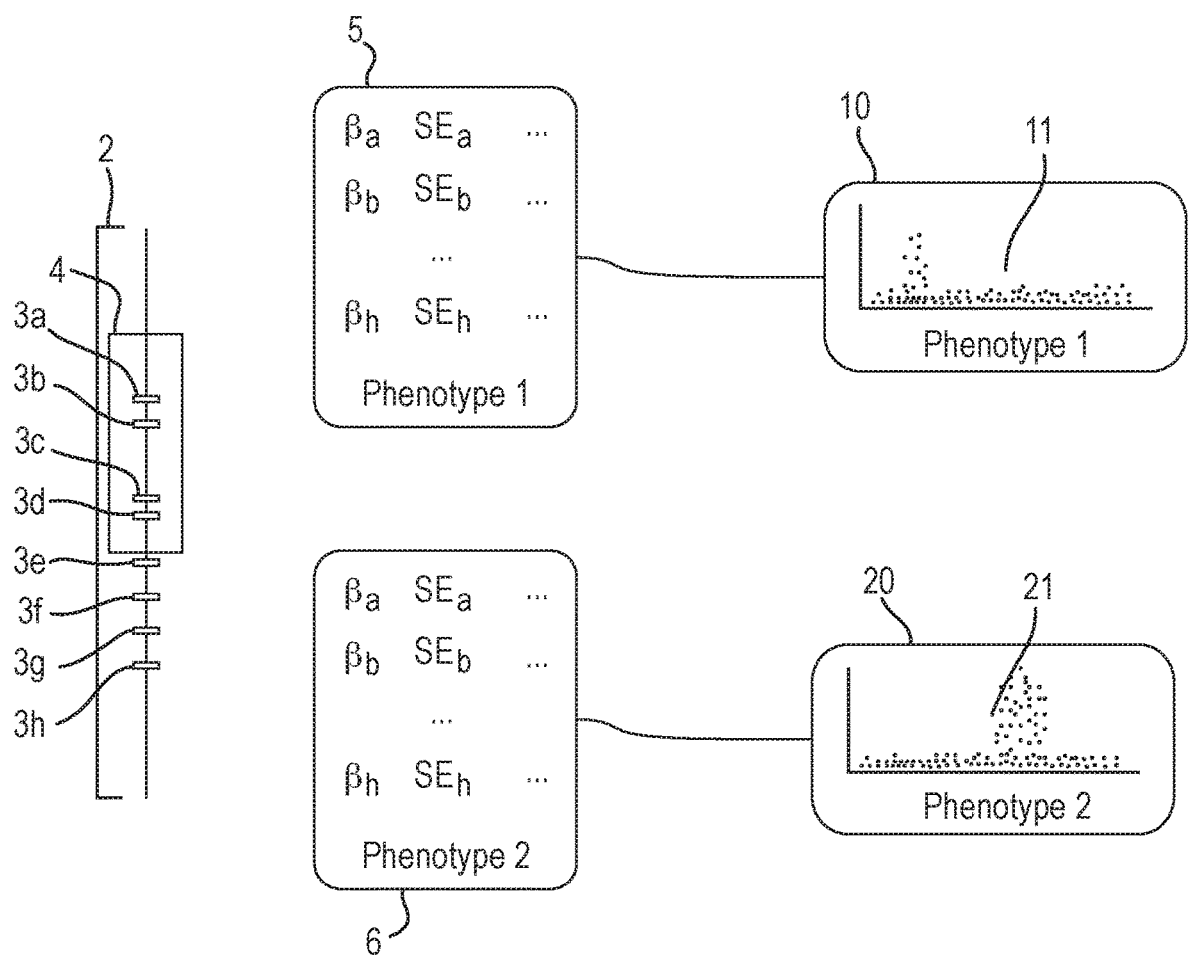
FIG. 2 shows genetic variants within a region of the genome, and a schematic of input units derived using information from studies.

The first part of the example embodiment comprises forming selected regions of the genome for analysis. Selected regions may be chosen arbitrarily. However, the formation of selected regions desirably strikes a balance between: (i) minimising the selected region size to avoid capturing multiple genetic variants that are causal for a single cluster; and (ii) maximising the selected region size to include all genetic variants that are correlated with each other so as to minimise the chance of falsely attributing causality to a genetic variant due to its correlation with other genetic variants outside the selected region. There are a number of ways to do this. In an alternative embodiment the selected region may be placed around a gene, or other functional part of the genome, that is of specific interest. Referring to FIG. 1, in the example embodiment, a selected region 2 includes a particular gene of interest 4 and includes a window of a predetermined number of base pairs (between $10^2$ and $10^{11}$ base pairs, e.g. 1 mega base pairs) around the gene. As shown in FIG. 2, the selected region 2 includes a plurality of genetic variants 3a-3h, some of which (variants 3a-3d) are within the gene of interest 4, and some of which (variants 3e-3h) are outside the gene of interest 4. In an alternative embodiment, selected regions 2 could be formed by tiling windows across the genome 1. The size of these windows could be determined, for example, by physical distance (that is number of basepairs in the region) or genetic distance (which is related to recombination rates). Another alternative would be to adaptively estimate changes in cluster assignment of phenotypes across the genome 1 for different choices of selected region 2.

The second part of the example embodiment comprises a method to generate a prior distribution on the number and/or size of the clusters. This example embodiment makes use of the distribution induced by the so-called Chinese Restaurant Process (CRP). Briefly, the CRP is a particular stochastic model for the assignment of successive units to clusters or groups in such a way that the number of groups is in itself random and not pre-specified[17]. This example embodiment extends the CRP through the addition of a single "null" cluster that has a pre-determined prior probability, p, while the other clusters induced by the CRP are jointly assigned the remaining prior probability (the CRP is the special case where p=0). Consequently the number of clusters is estimated from the data based on a CRP with prior parameter $\alpha$. An alternative method for generating a prior distribution is to fix the number of clusters and to assign prior probabilities through a Dirichlet distribution.

[17] Aldous, D. J. (1985). "Exchangeability and related topics". École d'Été de Probabilités de Saint-Flour XIII—1983. Lecture Notes in Mathematics. 1117. pp. 1-1. doi:10.1007/BFb0099421. ISBN 978-3-540-15203-3.

The third part of the example embodiment comprises a method to generate the likelihood function which describes the probability of the observed GAS summary-statistic data given an assumed cluster assignment of the phenotype of that GAS. This corresponds to determining the characteristics of an input unit.

Referring to FIG. 2, GAS 5, 6 contain at least summary statistic data $\hat{\beta}$, SE for the phenotype associated with the GAS. Each GAS 5, 6 is used to derive an input unit 10, 20, and the characteristics of the input unit 10, 20 comprise a set of metrics which quantify the strength of evidence for association in each input unit 10, 20 of each genetic variant 3a-3h in the selected region 2 being causal for the phenotype of the input unit 10, 20. The characteristics of an input unit may also comprise other functions of the input unit other than probability metrics. The inferred effect size $\hat{\beta}$ and the standard error SE of the inferred effect size are the most important of the GAS summary-statistic data used to derive an input unit 10, 20 in the example embodiment.

In the example embodiment, the likelihood function is chosen to be the per-variant likelihood of the summary statistics $\hat{\beta}$, SE. For genetic variants occupying a non-null cluster this is given by the alternative model ($H_1$: $\beta \sim N(0, SE^2+\sigma^2)$), and for genetic variants assigned to the null cluster this is given by the null model ($H_0$: $\beta \sim N(0, SE^2)$). In both cases, N(x, y) is a normal distribution with mean x and variance y. Instead of working directly with these likelihoods, the likelihood under a model is divided through with the likelihood under the null model to obtain a "scaled" likelihood. In the example embodiment, the scaled likelihood for the alternative model takes the form of a Bayes factor BF, so that the characteristics of an input unit used to determine the degree of similarity comprises Bayes factors of each of the plurality of genetic variants in the selected region being causal for the phenotype corresponding to the input unit. In the example embodiment, the Bayes factor is given by:

$$BF(SE, \sigma^2) = \frac{p(H_1)}{p(H_0)} = \frac{p(H_1)}{p(H_0)} = \sqrt{\frac{SE_i^2}{SE_i^2 + \sigma^2}} \exp\left(\frac{\hat{\beta}_i^2}{2} \frac{\sigma^2}{SE_i^2(SE_i^2 + \sigma^2)}\right).$$

The second equality is justified conditional on genetic variant i being causal, under the assumption that no other variants in the region are causal (see Maller et al.[18]); and see Wakefield[19] for the last equality. For the null model the scaled likelihood is simply a factor 1. As these Bayes factors only depend on $\hat{\beta}_i$, $SE_i$ they can be pre-calculated for each genetic variant included in each GAS. In the example embodiment, a 'marginalised' likelihood is calculated by marginalising over the causal genetic variant i using a prior distribution over the causal genetic variants. This means that in the example embodiment, input units are combined when calculating the characteristics of a cluster using a prior distribution of the likelihoods of each of the plurality of genetic variants being causal. In the example embodiment, a uniform prior distribution is used with equal likelihood for each genetic variant.

[18] Nat Genet. 2012 December; 44(12): 1294-1301.
[19] Gen. Epid. 33:79-86 2009

An alternative embodiment can incorporate additional information on which genetic variants are likely to be causal genetic variants in the selected region of the genome by incorporating an informative functional prior in the calculations that exploits functional annotations of genetic variants across a region instead of marginalising over a uniform prior distribution. If an informative functional prior is used, the prior distribution of the likelihoods incorporates pre-existing information about variation in functionality relevant to causality over the genetic variants. Functional priors are known in other approaches; for instance the PAINTOR method[20], but have not before been applied to a method of the type described here.

[20] PLoS Genet 10(10): e1004722

Under the assumption that all genetic variants have full information about their association in each GAS, then the marginalised likelihood is a sum over the BF at each genetic variant weighted using the prior distribution of the probability that each variant is the causal variant.

The fourth part of the example embodiment comprises a method for the meta-analysis of GAS assigned to a cluster in order to calculate the probability that each genetic variant is a causal genetic variant. This comprises calculating the characteristics of the cluster by combining input units assigned to the cluster. In the example embodiment the GAS are assumed to be independent, and the effect sizes are assumed to be uncorrelated, so that the evidence can be accumulated across GAS as a product of the Bayes factors calculated for each GAS. Then calculating the characteristics of a cluster comprises calculating a product of the Bayes factors of the input units assigned to the cluster. All this combines to the full cluster likelihood, which represents the likelihood of a cluster given the GAS that have been assigned to it. In the example embodiment, this is calculated as follows.

Let $BF_{ij}=BF(SE_{ij},\sigma^2)$ be the Bayes factor associated to variant i and GAS j, and let $C_s$ be the set of GAS assigned to cluster s, where $C_0$ denotes the GAS assigned to the null cluster (which are considered to not carry causal genetic variants in the selected region). Let K be the number of (non-null) clusters, let $k=(|C_1|, \ldots, |C_K|)$ be the vector of cluster sizes, and let N be the total number of GAS. Finally, let p and $\alpha$ be parameters of the prior distribution of the number and size of clusters, where the parameter p determines the prior probability that a GAS is assigned to the null cluster and therefore is assumed to carry no causal genetic variant in the selected region. Firstly, the aggregate evidence for genetic variant i being causal for the set of phenotypes of cluster s is defined as:

$$\text{meta}_{is}=\Pi_{j \in C_S} BF_{ij},$$

with the understanding that $BF_{i0}=1$ so that $\text{meta}_{i0}=1$. Then, the full cluster likelihood becomes:

$$L=p^{|C_0|}Pr(\alpha)\Pi_{s=1}^{K}(\Sigma_i Pr(i)\text{meta}_{is}).$$

Here Pr(i) is the prior distribution for genetic variant i being causal in a cluster, which in the example embodiment is the uniform distribution (that is $$Pr(i) = \frac{1}{G}$$

where G is the number of genetic variants in the selected region). Finally, in the example embodiment, $Pr(\alpha)$ is the Chinese Restaurant Process prior with concentration parameter $\alpha$, or explicitly:

$$Pr(\alpha) = \frac{\Gamma(\alpha)}{\Gamma(\alpha + |k|)} \alpha^K \Pi_{i=1}^{K} \Gamma(k_i),$$

where $|k|=k_1+k_2+ \ldots +k_K=N-|C_0|$.

The fifth part of the example embodiment is the process by which GAS are assigned to clusters. Input units derived from GAS are assigned to clusters by determining a degree of similarity between characteristics of the input unit, and the characteristics of a cluster. This degree of similarity may be used to determine the probability of assigning the input unit to the cluster. In the example embodiment, each GAS j is initially assigned to the null cluster. Then, a Markov chain Monte Carlo algorithm is used which considers each GAS j in turn, removes it from its current cluster, and computes the prior and likelihood of assigning it to: (i) the null cluster; (ii) a new cluster; and (iii) each of the existing clusters. The algorithm then stochastically makes a new assignment with a probability proportional to the likelihood of GAS j's assignment to each of the clusters described in (i) to (iii) immediately above. After the input unit is assigned, the characteristics of the cluster to which it is assigned may be recalculated.

In more detail, in the example embodiment, a GAS j under consideration is first removed from its current cluster s (if it is assigned to a cluster other than the null cluster), and the characteristics of that cluster $\text{meta}_{is}$ are recalculated for the GAS that remain assigned to that cluster. Next, the degree of similarity is calculated, which in the example embodiment is the likelihood of assigning study j to any existing cluster s', a new cluster s''=K+1, or the null cluster (s'=0). The likelihood for each of these possibilities is:

Null cluster: $p$;

New cluster $s'' = K+1$: $\frac{(1-p)\alpha}{|k|-1+\alpha}\sum_i BF_{ij}Pr(i)$;

Existing cluster $s'$: $\frac{(1-p)k'_s}{|k|-1+\alpha}\sum_i BF_{ij}\frac{Pr(i)\text{meta}'_{is}}{\sum_i Pr(i)\text{meta}'_{is}}$.

In the example embodiment, one of these possibilities is then chosen with a probability proportional to the likelihood of that possibility. Some embodiments may not include the null cluster, which in the above equations would be equivalent to setting p=0.

The algorithm described above is executed iteratively by repeating the assignment of each study a set number of times, for example between 100 and 1,000,000 times, but typically 10,000 times, or until a predetermined convergence threshold is reached. The output can then be used to describe the assignment of studies to clusters and the information about possible causal variants, and potentially the confidence in the quantities. These outputs can be used directly to identify shared biological mechanisms.

After the Markov chain Monte Carlo algorithm has stopped as a result of reaching a pre-set convergence criterion or after a predetermined number of iterations, the cluster assignments at each iteration of the algorithm can be post-processed to provide a single cluster assignment in various ways. In the example embodiment the algorithm is run for a fixed number of iterations and the final study assignment is based on the assignment at the last iteration of the Markov chain Monte Carlo algorithm. Other natural possibilities are, for instance, averaging appropriate quantities, such as co-occurrence of clusters, over a subset of the steps of the chain, and using these to determine final cluster assignments. Another way is to calculate the frequency with which each cluster pair shares a cluster, and form clusters that maximise the within-cluster sharing frequency and minimises the between-cluster sharing frequency.

Figure 3:
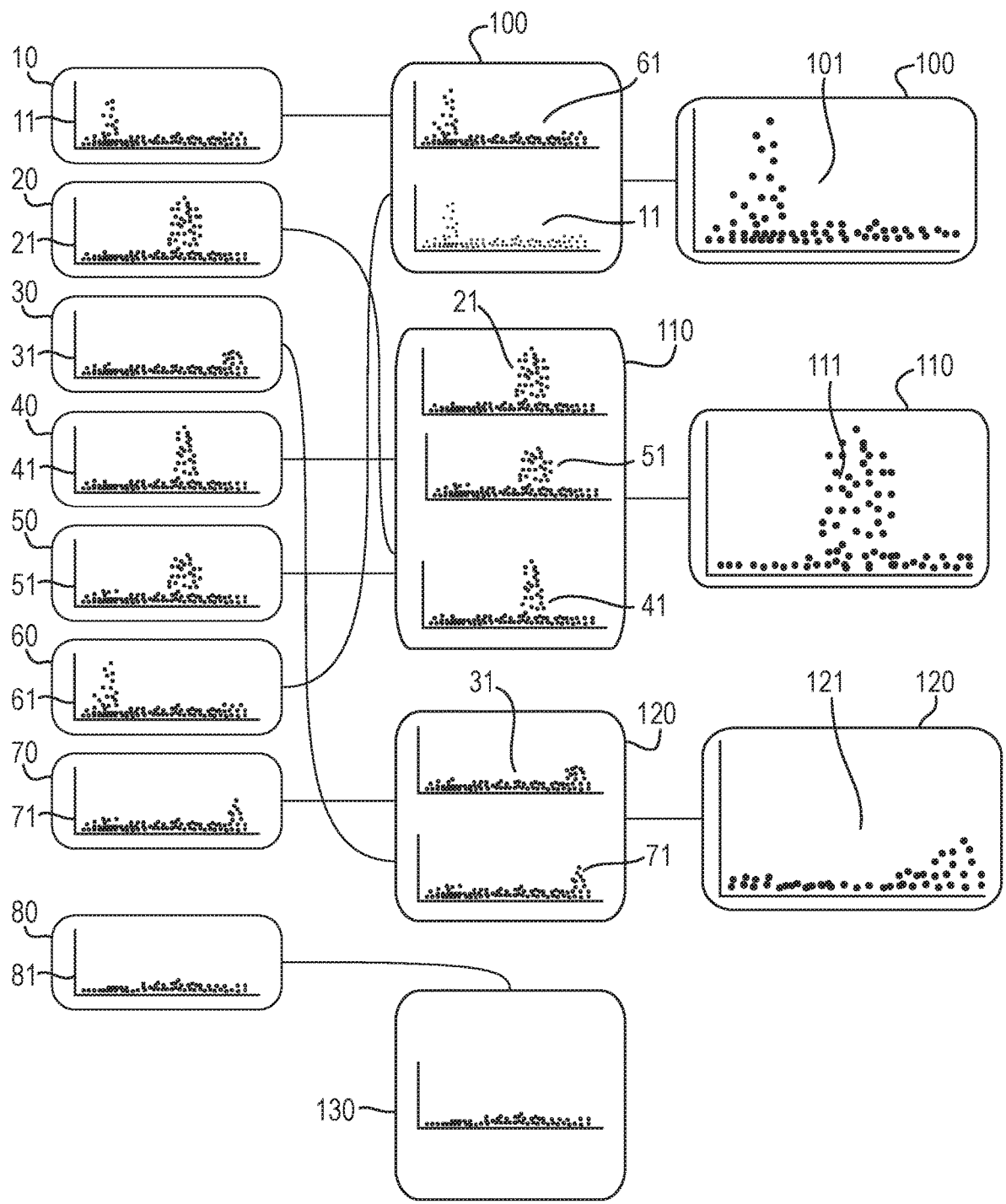
FIG. 3 shows a schematic of the assignment of input units to clusters in an embodiment.
Figure 4:
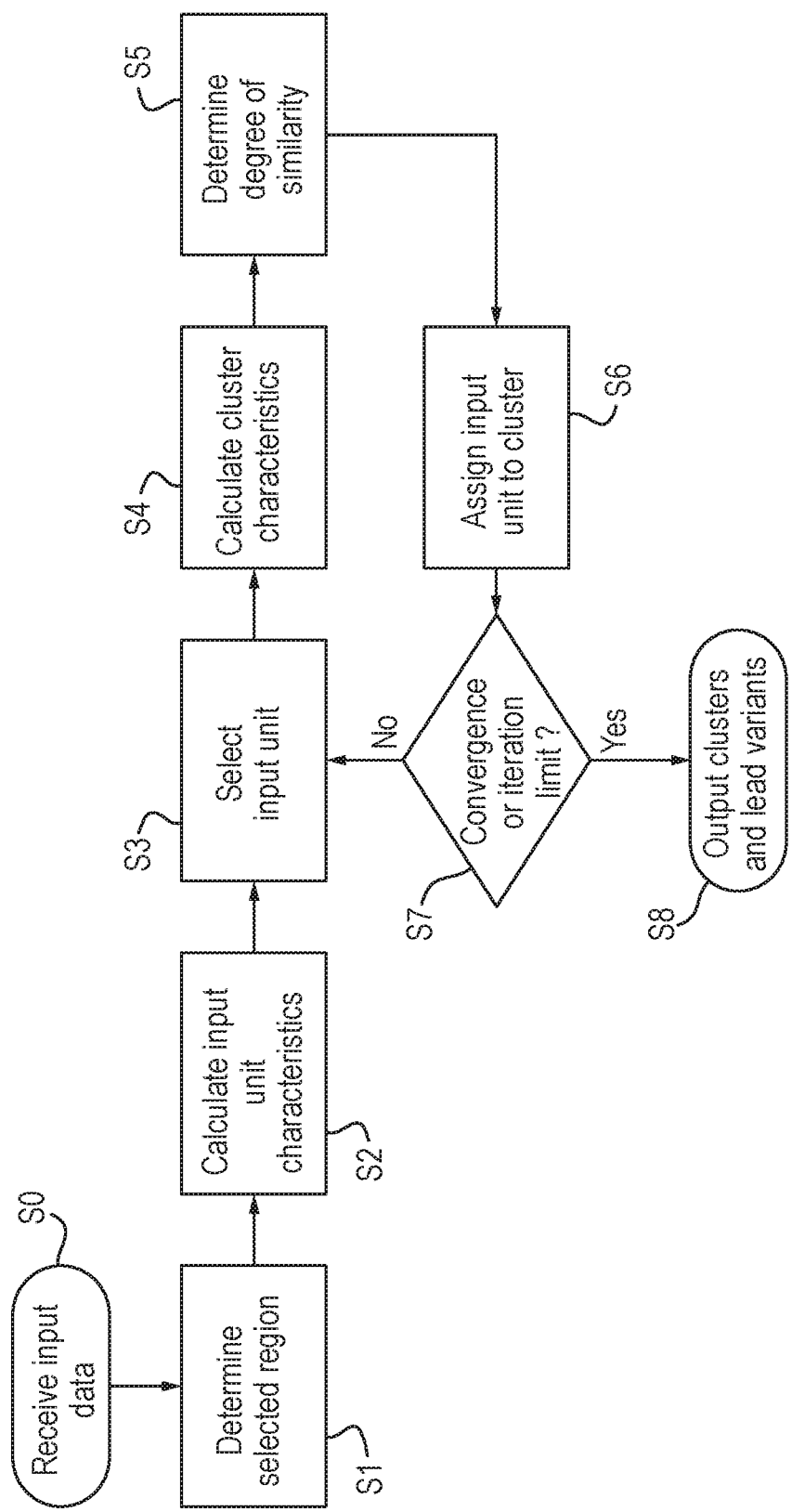
FIG. 4 shows a flow diagram of steps in an embodiment of the method.

The assignment of the studies to clusters in the example embodiment can be visualised referring to FIGS. 3 and 4—where FIG. 3 characterises a possible realisation of the algorithm summarised in FIG. 4. In step S0 of FIG. 4, input data comprising a plurality of input units 10-80 (as in FIG. 3) is received. In step S1, a selected region 2 is determined containing a plurality of genetic variants 3a-3h (as in FIG. 2). In step S2, sets of characteristics 11-81 (as in FIG. 3) are calculated for each of the plurality of input units 10-80. For each of the sets of characteristics 11-81, each point shows association of one of the plurality of variants with the phenotype corresponding to the input unit, where the x-axis shows location of the variant within the selected region 2 (as in FIGS. 1 and 2), and the y-axis shows strength of association. In step S3, input unit 10 with characteristics 11 is selected. Initially, no non-null clusters are formed, so no cluster characteristics are calculated. In the example realisation shown in FIG. 3, input unit 10 is assigned to a new cluster 100. The process returns to step S3, where input unit 20 with characteristics 21 is selected. A set of characteristics 101 is calculated for cluster 100 based on the characteristics 11 of input unit 10 assigned to cluster 100. The degree of similarity between the characteristics 21 of input unit 20 and the characteristics 101 of cluster 100 is small, so input unit 20 is also assigned to a new cluster 110. Steps S3 to S7 are repeated until a predetermined convergence threshold is reached or a predetermined number of iterations is performed.

At the conclusion of the assignment process, input units 10-70 are assigned to clusters 100, 110, and 120. For example, in FIG. 3, input unit 80 is assigned to the null cluster 130. The sets of characteristics 101, 111, 121 of the clusters 100, 110, 120 are calculated from a combination of the sets of characteristics 11-71 of the input units 10-70 assigned to each cluster. For example, the set of characteristics 111 of cluster 110 is formed from a combination of the sets of characteristics 21, 41, and 51 of input units 20, 40, and 50. FIG. 5 illustrates using the set of characteristics 111 of cluster 110 to determine the lead variant 112, which is most likely to be causal for the cluster 110.

An output of the method is illustrated in FIG. 6, displaying associations of the lead variant 112 with traits (including gene expression measures and other phenotypes) identified as members of cluster 110. Effects estimates 202 to the right of the central null line 200 indicate a positive association with lead variant 112, and effect estimates 201 to the left indicate a negative association with lead variant 112. Bars on the effects estimates indicate uncertainty. The bars 210 indicate for each trait the magnitude 221 of the posterior probability of membership of cluster 110 and the magnitude 220 of the posterior probability of membership of the null cluster 130 (the posterior probability of assignment to other clusters 100 and 120 is assumed to be approximately 0 in FIG. 3). These characterise the certainty around cluster assignment, and can be determined using the output of the Markov chain Monte Carlo algorithm.

The choices in the example embodiment allow particularly efficient calculation at each stage of the assignment process. In particular, the (scaled) likelihood of genetic variant i being causal for a cluster of GAS is simply the product of the Bayes factors calculated using those GAS; the full likelihood is then obtained by marginalising over i using these (scaled) likelihoods and a prior distribution over genetic variants.

This efficiency increases the extent of the data that can be analysed using this method. Existing methods are only able to analyse data from, at most, around a dozen GAS simultaneously. Embodiments of the present disclosure, in contrast, are fully scalable and can take into account data from many thousands of GAS, across the full range of available phenotypes.

Additionally, existing methods do not attempt to explicitly cluster phenotypes and identify one or more lead variants in a selected region of the genome, but instead base their inference on a "causality matrix" C, where $C_{ij}$ is 1 if genetic variant i is causal for phenotype j. Such a method only encodes the clustering implicitly and is computationally harder to analyse.

Figure 7:
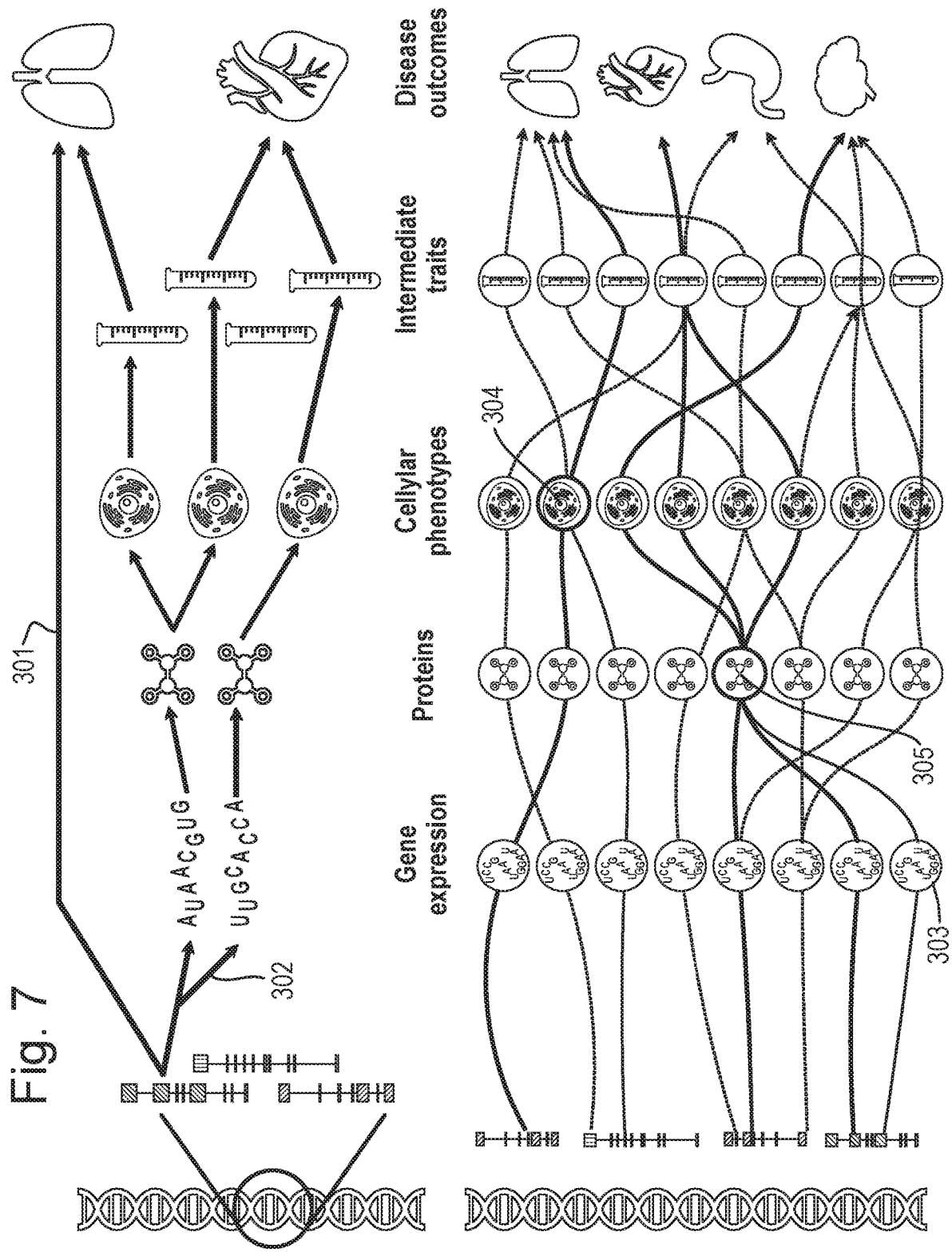
FIG. 7 shows a comparison between prior art methods and an embodiment of the disclosure.

A visual comparison between the present method and previous methods is given in FIG. 7. Conventional genome wide association analyses 301 identify genetic variants associated with disease risk. They rarely, however, offer insights into the gene truly responsible for the observed association, its underlying biological mechanisms or targets for potential pharmacological modulation. Comparisons 302 between genetic association analyses of a range of traits can offer some mechanistic insights. These are often hampered, however, by analytical challenges in distinguishing discrete biological pathways. As such, the observations can be misleading. Analysing large number of traits together using embodiments of the present disclosure 303 allows mechanistic steps to be grouped and ordered in their respective pathways. In doing so, biological "pressure points" 304 and 305 (features of pathological pathways closely involved in disease aetiology that may represent valuable therapeutic targets) can also be identified.

The enhanced efficiency and power of embodiments of the present disclosure confer significant advantages compared to known methods. Crucially, the method is able to identify large numbers of sets of different related and unrelated association signals within the region. For example, it is beneficial to jointly consider phenotypes such as levels of gene expression, protein expression, biomarkers, and disease endpoints in the same cluster when these phenotypes are all causally driven by the same genetic variant. In addition, it is beneficial to separately cluster phenotypes causally associated to different genetic variants in the same selected region of the genome. These two aspects are of particular relevance to the analysis of thousands of GAS, due to the increased chance of related and unrelated associations occurring in the same selected region.

Consequently, the ability of embodiments of the present disclosure to cluster such a broad range of GAS within a region, means that it can be used to: (i) establish a causal, mechanistic relationship between phenotypes within a cluster (i.e. to demonstrate a mechanistic link or identify a biological pathway); (ii) identify and discern mechanistically independent overlapping associations between genetic variants and many phenotypes of interest, which otherwise may have been considered to be acting through the same mechanistic relationship; and (iii) identify real associations from weak signals of association between genetic variants and phenotypes of interest by identifying similarities in the pattern of association that would be missed by thresholding-based approaches applied to the individual weak association signals that do not form clusters as in the present method.

The breadth and nature of the range of potential inputs to the present method is such that the user can have confidence that the outputs will present a very full picture of the relevant biology. Consequently, the outputs, which can include the identification of phenotypes that share underlying biological mechanisms, and/or the identification of lead variants for a cluster of phenotypes, can be used for many different, valuable applications, all of which could make use of the inputs (typically the genetic information about an individual) and also, more broadly, could leverage the outputs (i.e. detailed information about biological mechanisms).

Foremost of the method's applications is its ability to generate a detailed understanding of the relationship between different genes, cells, tissues, molecular mechanisms, and biological pathways in an organism. The outputs allow the user to, for example, learn that when a particular gene is perturbed in some way specific consequences are highly likely to ensue, and that this allows valuable conclusions about related diseases and conditions to be drawn. Many subsequent applications of the method take these complex biological insights into account.

Figure 8A:
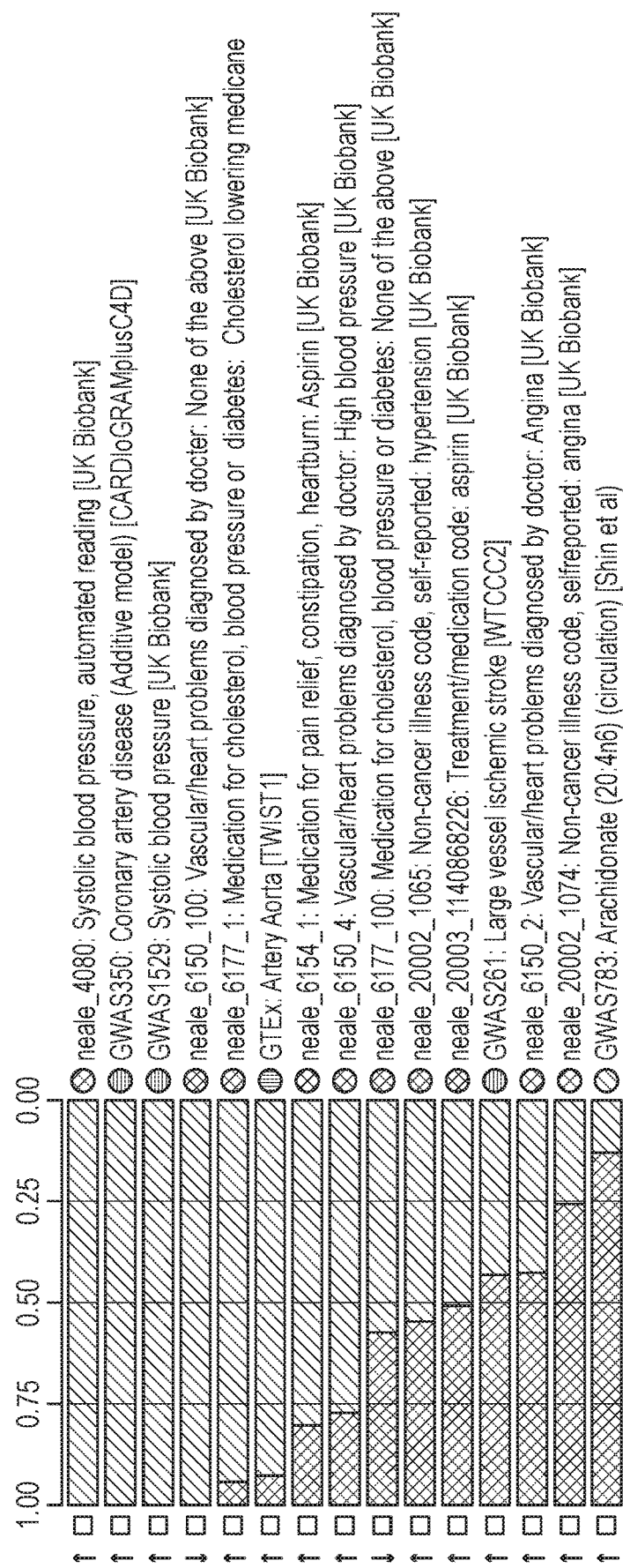
FIG. 8 shows an example output of an embodiment of the method using previously published GAS data.
Figure 8E:
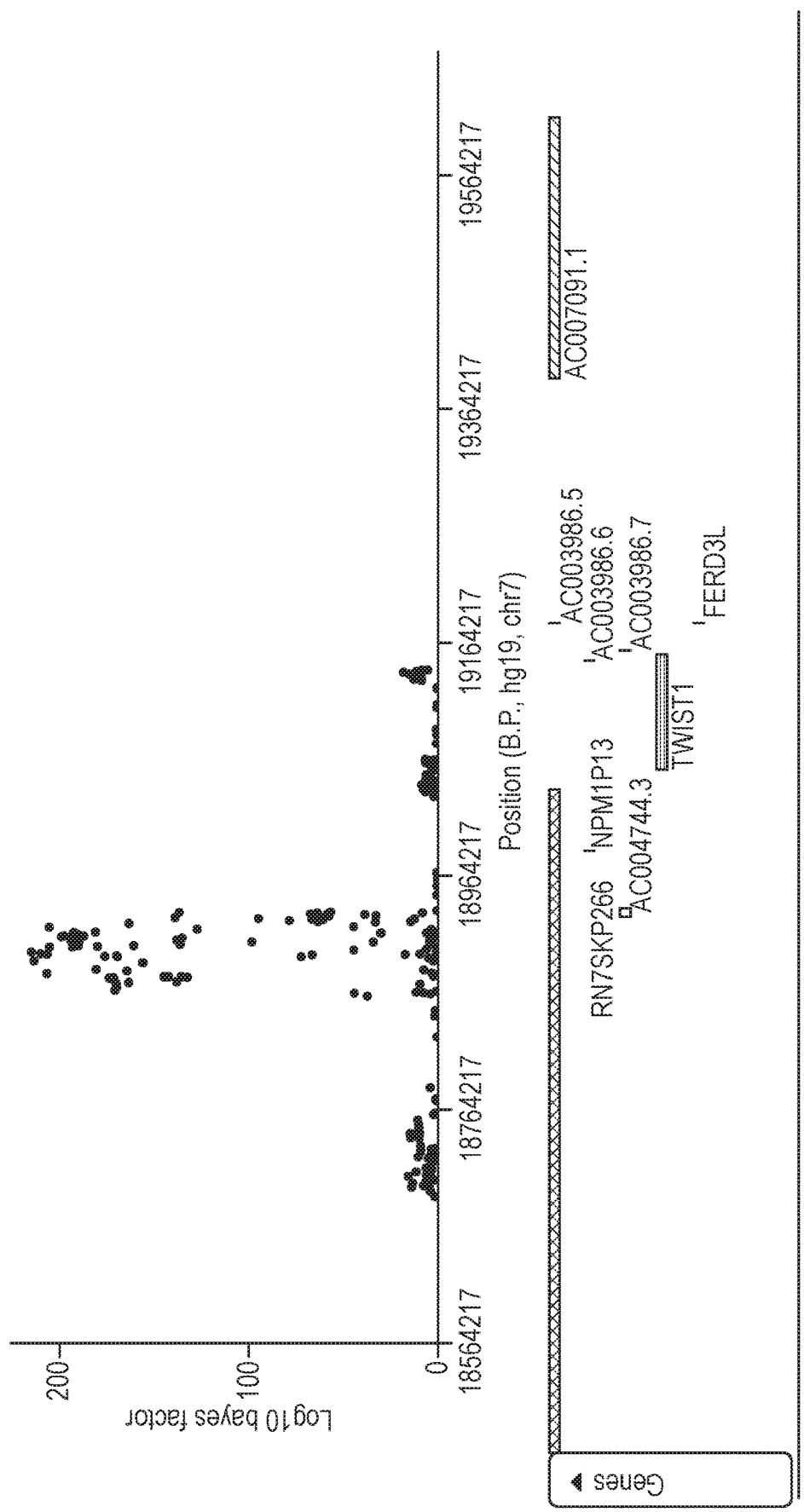
Figure 8F:
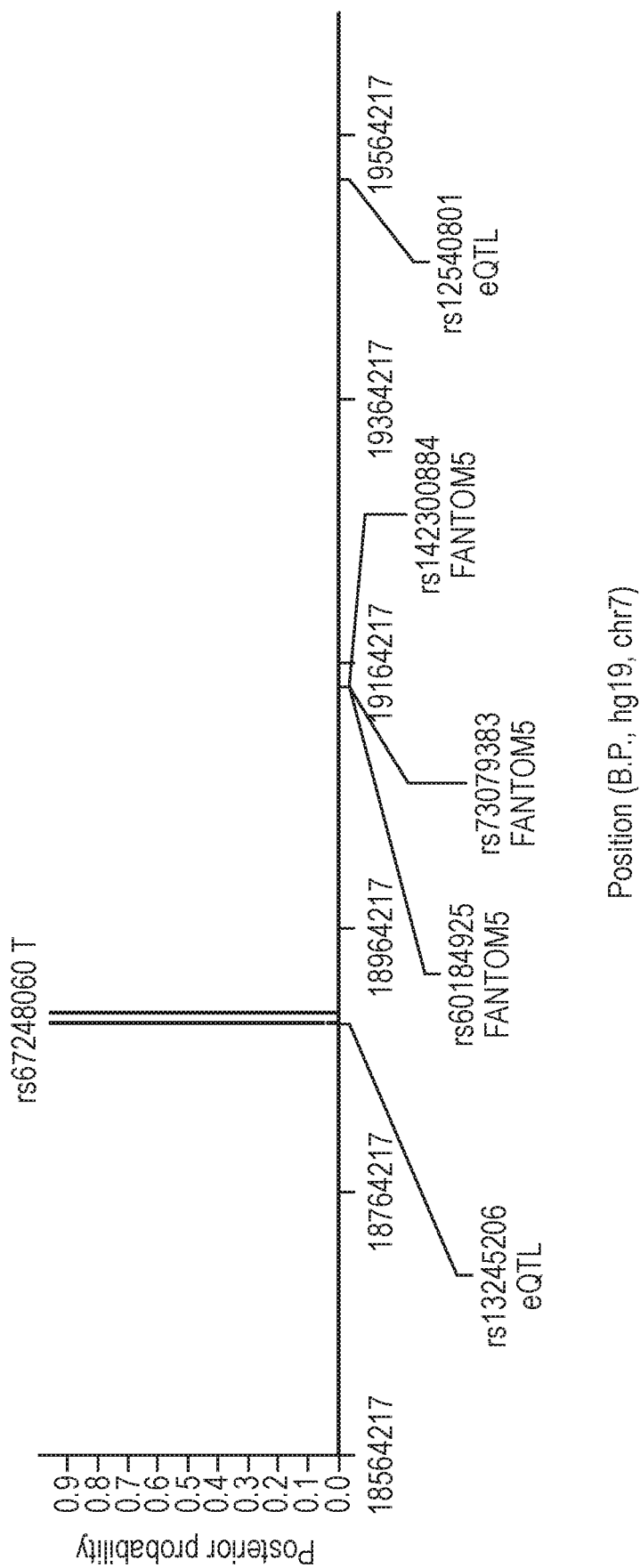

In an example illustrating the ability of the method to uncover such biological insights, FIG. 8 describes the results of applying the previously described example embodiment to data on thousands of previously-published GAS. In the region around the TWIST1 gene, a plurality of clusters are identified by the example embodiment, including two distinct clusters that link to TWIST1. The traits that are found with high probability to be members of the first cluster are displayed in FIG. 8a (the scale at the top gives the posterior probability of cluster membership for each trait). The meta-analysis across the traits that are members of this cluster generates a combined signal plot that is displayed in FIG. 8b (the y-axis scale gives the $\log_{10}$ Bayes Factor for association at each common variant in the region), and this in turn generates a set of credible causal variants which has the variant rs2107595 as its principal member (FIG. 8c). Traits that are found with high probability to be members of this cluster include systolic blood pressure and risks of coronary artery disease, hypertension and large vessel ischemic stroke (recall that no background about the phenotypes is used in the clustering). Another trait of interest in this cluster is the level of expression of the gene TWIST1 in the aortic artery.

This analysis thus provides substantial evidence that levels of TWIST1 in the vasculature play a causal biological role in the risk of each of coronary artery disease, hypertension and large vessel ischemic stroke. The arrows on the left of FIG. 8a also indicate the direction of effect: increasing levels of TWIST1 in the vasculature are implicated in increasing risk of all three conditions. In contrast, extensive studies of this genomic region, following its identification as a risk locus for large vessel ischemic stroke in 2012[21], had failed to pinpoint the causal gene. Having established TWIST1 as the likely causal gene, a plausible mechanism for its action is provided by a more recent study[22] showing that TWIST1 plays a role in endothelial proliferation as a vascular response to shear stress.

[21]Nat Genet. 2012 February; 44(3): 328-333.
[22]Circ Res. 2016 July; 119(3):450-62

As a further illustration of the ability of the method to uncover complex biological insights, FIG. 8d displays the traits that belong with high probability to a separate cluster identified in the same region around the TWIST1 gene. The meta-analysis across the traits that are members of this cluster generates a combined signal plot that is displayed in FIG. 8e, and this in turn generates a set of credible causal variants which has the variant rs67248060 as its principal member (FIG. 8O. Traits that are found with high probability to be members of this cluster include male pattern baldness, as well as expression levels of the gene TWIST1 in the brain and thyroid.

In summary, the analysis described in FIGS. 8a-8f illustrates the ability of the method to uncover new biological insights. The analysis explains the biology driving the previously published stroke GAS signal, links it with other cardiac phenotypes, and provides an example of tissue specific regulation of the same gene with different biological consequences. All these observations are new. These observations also provide a clear therapeutic hypothesis: that decreasing levels of TWIST1 protein in the vasculature would be a desirable target and mode of action for a drug to treat coronary artery disease, hypertension and large vessel ischemic stroke.

The method is particularly well suited to the discovery and development of therapeutics, particularly for the treatment of humans. Outputs of the method can be used to propose, support, and verify full or partial hypotheses that can underpin drug target discovery, drug target validation, and drug reformulation and repurposing projects. Such hypotheses may include therapeutic hypotheses e.g. inhibiting a named gene or its product will have a certain set of biological consequences, which will in turn be helpful for the treatment of a named disease. Similarly, the method can be used to aid the investigation of drug-drug interactions, on target safety effects, the identification of biomarkers, patient selection, clinical trial design, the stratification of human patients in clinical trials, and dosage regimes.

Embodiments of the present disclosure can be applied to any setting in which it is of interest to understand the relationship between an organism's genotypes and the traits and phenotypes which it exhibits over its lifetime. In humans, information about the relationship between an individual's genotypes and traits may be of intrinsic interest and provided directly to individuals. The information may be relevant to their wellness and lifestyle choices.

Embodiments of the present disclosure can also be applied to more clinical settings. The method can be used to improve calculations made to predict an organism's chances of developing a particular disease, or condition, or any other phenotype of interest. Further clinical applications of the invention are possible, such as using the inputs and outputs of the method to assist physicians with patient management, at individual or cohort level. Specific uses in healthcare of prediction of traits from genetic variation include, but are not limited to, stratifying individuals on the basis of their risk of developing a specific disease; aiding diagnosis of disease, or identification of disease subsets; informing on the best behavioural or medical interventions; improving screening programs; improving reference distributions against which to compare individuals; and selecting individuals to participate in clinical trials. In each case, embodiments of the present disclosure have application at the level of an individual, a cohort, or a population. They may apply in the context of a specific trait or disease of interest, but could also apply to any set of clinical or biological events that constitute the natural history of an individual or organism.

Information about an individual's risk of developing diseases or exhibiting traits could be used in other settings including: in calculating insurance premiums; in pre- and post-implantation diagnosis; in targeting goods, services or opportunities to individuals; or indeed in any setting in which a trait of interest has a genetic basis, and in which information on an individual's genotypes are available.

An example embodiment would use the method to estimate the causal variants and effect sizes for a phenotype of interest (target phenotype), and use these to calculate a prediction based in an individual's genotypes. For example this could be achieved by:

1. Applying the method genome-wide on a large number of studies, including but not limited to the target phenotype, in order to identify one or more causal variants (or posterior distributions on causal variants).
2. Estimating the effect sizes at these identified variants, or variants with high posterior probability, across the studies relevant to the target phenotype. These may be improved by adjusting for the correlation in the effect size estimates between studies and causal variants as appropriate.
3. Obtaining the genotypes of an individual for which a calculation of the genetic contribution to the phenotype is to be made.
4. Calculating the contribution of the causal variants to the target phenotype on the basis of the estimated effect sizes at these causal variants and the individual's genotypes. One approach is to appropriately combine the effect sizes associated with the alleles they carry at each causal variant, or to average this over the posterior distribution of causal variants and their effects. The measure which represents the combination of these effects on an individual's risk is sometimes referred to as a polygenic risk score (PRS).
5. To use the PRS as a quantitative measure of risk (for example as an estimate of the relative risk compared to a typical individual) or to assess its position with an appropriate cohort (for example an individual may identified be in the top 10% of the empirical distribution across individuals).

In another example embodiment, the estimation of effect sizes is built on studies with a diverse range of ethnicities. The benefit from such an approach is two-fold. Firstly, it refines the inference of the set of causal variants that impact the target phenotype. Secondly, the effect size estimates combine the values from each of the independent populations, hence providing population specific estimates for the target phenotype that are made more accurate by the partial sharing of genetic effects across populations.

In another example embodiment, the estimation of effect sizes for a predictive model takes advantage of studies of different, but related, traits. A correlation matrix, or a collection of correlation matrices, can be inferred between traits from the data using genome-wide information. These genome-wide estimates can then be used to refine the estimation of effect sizes for studies of interest at each causal variant. The final aim being to obtain more precise effect size estimates that translate into more accurate predictions. The utility of applying the methods described herein is that they allow all the input studies to contribute to the identification of clusters, and therefore causal variants, and allow estimation of the true causal effects across studies which are inferred to share variants.

In another embodiment the genetic predictions described above may be integrated with, and adjusted for, other important covariates including, but not limited to: demographic information (e.g. age, gender, height); summaries of genetic background (e.g. ancestry, homozygosity, further measures of polygenic risk); and potentially targeted analysis of specific regions of the genome (e.g. the Major Histocompatibility Complex) where there is existing information on the relationship between genetic variation and traits of interest.

If clinical data are available for a cohort of individuals for whom the genetic contribution to a phenotype has been calculated then it is also possible to empirically calibrate the increase in risk of a particular clinical event for any given (possibly adjusted) genetic prediction. In another example embodiment genetic predictions (such as PRS) can be combined with any other data about an individual which is informative about future events that are of interest. For example, in a clinical setting genetic information, such as PRS, can for part of a broader set of biomedical data that is used to predict future health-related events.

In particular, the measurements provided by a screening test could be interpreted in the context of an individual's genetic risk for the disease in question, hence prioritising for further clinical investigation those individuals with screening scores close to the threshold and with high genetic risk. Similarly, screening could be prioritised for high risk individuals based on their genetic score. This could be achieved by using genetic risk to calculate the prior likelihood of developing a target disease and then using screening data through to calculate the posterior probability of disease status.

By combining these other types of clinical and/or genetic data about an individual with the previously determined contribution from the genotype, it is possible to improve a determination of the particular individual's present or possible future phenotype.

The example embodiment may be used in combination with other methods that leverage information about the relationship between genetic variation and phenotypes of interest, either through association evidence or by linking information about the function of the genome.

Of particular importance to the specific example application of understanding human biology and treatment of human disease, is generating results that, without using the present method, would only have been possible through direct in vivo experimentation, which may require invasive means. This is possible because the input data—which (when the organism under investigation is human) will ultimately have been drawn from human research participants—can be analysed on a scale that is beyond the capability of other methods.

In some embodiments the method includes identifying two or more causal genetic variants for each of one or more clusters of phenotypes within a selected region. This involves considering the correlation between genetic variants within the region, usually summarised by the "LD matrix", the matrix of correlations $r_{ij}$ of genotypes $g_i$, $g_j$ at locations i, j, often obtained from subpopulations of a reference panel such as the 1000 Genomes consortium, or the Haplotype Reference Consortium. The only change needed under this assumption is to use a different likelihood calculation. The appropriate likelihood required follows methods similar to the FINEMAP method[23], but adapted to the present method.

[23] C Benner et al., FINEMAP, Bioinformatics 2016

One such embodiment would include a first step to identify a first genetic variant that likely is causal (i.e. a first lead genetic variant) for the phenotypes in the cluster as outlined above. In a second step, the method will consider, in addition to every single variant as potentially being a causal genetic variant for the phenotype, also pairs of variants, consisting of the first genetic variant identified in the first step, combined with any other genetic variant in the region, as both being causal genetic variants for the genotype. This approach can be further extended by including third, fourth etc. potentially causal variants (i.e. further lead genetic variants) in subsequent steps. This stepwise approach has the advantage that it avoids the need to consider all pairs (triplets, quadruplets, . . . ) at once, which would be computationally more expensive, although still feasible in some contexts.

Another such embodiment would identify additional causal variants by updating the summary statistics to account for the effect of causal variants already identified within a cluster, and then assessing the residual evidence for an additional causal variant. The approach can be applied iteratively to explore the space of causal variants within or across clusters by proposing the addition or removal of at most one causal variant. Such approaches exploit results on the distribution of observed effect size estimates given a set of causal variants with effect sizes α:

$$\text{MVN}(\hat{\beta}; SRS^{-1}\alpha, \Sigma)^{24}. \tag{1}$$

in which S and R are the variance and the correlation of the alleles for which the effect sizes estimates $\hat{\beta}$ are assumed to be drawn, and $\Sigma$ describes the covariance in these estimates. Non-zero elements of the vector α indicate variants assigned to be causal (in the basic embodiment only one of these are assumed to be non-zero). Residual evidence for association can be obtained by subtracting the effect of these variants so, for example, the residual effect size estimates are $\hat{\beta}' = \hat{\beta} - SRS^{-1}\alpha$. These can be used to calculate equivalent Bayes Factors at each variant. If a new causal variant, i, is identified then an estimate of its effect size, $\alpha_i$ is readily obtainable as the most likely estimate or by sampling from its posterior distribution, either of which could incorporate prior information on effect sizes as described above (for example by assuming the true effect size distribution to be Normal with mean 0 and variance $\sigma^2$). When assessing the cluster assignment of a study the MVN($\hat{\beta}$; SRS$^{-1}\alpha,\Sigma$) density can be calculated for only the non-zero elements of the vector $\alpha$.

[24]Ann. Appl. Stat. Vol. 11, Number 3 (2017), 1561-1592 (https://projecteuclid.org/euclid.aoas/1507168840)

A further alternative embodiment could be used if for each GAS the summary statistics are not equally informative. This may occur for various reasons including: (i) occasional missing data resulting from problems at the genotyping stage; (ii) the necessity to impute certain genetic variants that were not measured or were insufficiently well measured at the genotyping stage for a particular GAS; and (iii) the varying level of imputation quality across the genome due to fluctuating levels of linkage disequilibrium (LD) between the focal genetic variant and nearby "tag" genetic variants. In an extreme case where a particular genetic variant i is not observed or imputed at all in GAS j, this GAS will not be selected to participate in a cluster that is characterised by having lead variant i, even when GAS j in fact is driven by variant i and the summary statistics at linked genetic variants are consistent with this. In this case additional information about the association between genetic variants and the phenotype of the input unit can be added to one or more of the input units by modelling the association between the one or more genetic variants and the phenotype corresponding to the input unit. For instance, the expected $\beta$ of study j can be modelled under the assumption that genetic variant i is causal, rather than the strength of the evidence that $|\beta_i|>0$ as is done in the example embodiment above. This is achieved by modeling the vector $\hat{\beta}$ given $\hat{\sigma}^2$ and the LD matrix $\Sigma$ under the assumption that genetic variant i is causal.

In such an embodiment addressing differential information, for a given genetic variant i that is being tested for being causal, it will be required to identify another variant j that is most informative about the genotype status of variant i. This can be quantified as the expected log Bayes factor for the model where i is causal as opposed to the model where i is not causal, where the expectation is taken over the values of the observed statistics under the causal model, and a model describing the incomplete observation process. With a particular choice of observation model, this expectation is, to first order, a function of $pr^2$ where p is the fraction of observed genotypes and $r^2$ is the i, j-entry of the LD matrix $\Sigma$, in such a way that maximizing $pr^2$ maximizes the information that genetic variant j provides about the genotype of genetic variant i.

Another such embodiment would apply the likelihood function by first adjusting GAS summary statistic data based on information about the true correlation in effect sizes $\hat{\beta}$ and/or the accuracy with which they are measured. The adjusted summary statistics can be obtained by defining a joint model for the observed data, the GAS-summary statistics, and the true effect sizes and their uncertainty in an idealised version of the original study: $\beta^*$ and SE*. The joint distributions can be approximated by multivariate normal distributions from which estimates of true effect sizes in the original study can be made. These can then substitute the original $\hat{\beta}$, SE in the likelihood. One approach is achieved by a singular value decomposition of the matrix $\Sigma=UDU'$ (because $\Sigma$ is symmetric) in equation (1) to obtain a multivariate normal density with a diagonal covariance matrix: MVN($D^{-1/2}U'\hat{\beta}$; $D^{-1/2}U'SRS^{-1}\alpha,I$). This is the form of a standard regression with independent observations and unit variance, where $Y=D^{-1/2}U'\hat{\beta}$ and $X=D^{-1/2}U'SRS^{-1}$ so that adjusted summary statistics can be obtained using Ordinary Least Squares estimates marginal for each variant so that for variant i, $\beta_i^*=(X_i'X_i)^{-1}X_i'Y$ and $SE_i^*=1/(X_i'X_i)^{-1/2}$. These calculations can be done efficiently for all variants jointly using matrix operations.

A further alternative embodiment optimises segmentation of the genome to form selected regions. Selected regions can be formed from tiles created by tiling the genome with a fixed number of either non-overlapping abutting tiles or partially overlapping tiles that minimise the correlation of genetic variants between tiles. The minimisation can be achieved by a dynamic programming algorithm. Another approach to optimising segmentation considers the process of segmentation as a "multiple change-point process", and uses a dynamic programming algorithm to efficiently consider all, or a large number of, possible segmentations. A preferred implementation uses a particle-filter based algorithm to implement this dynamic programming algorithm as a hidden Markov model with a sparse selection of supporting states, for example as described in Fearnhead et al[25]. Such an algorithm requires a likelihood of the observations given a particular segmentation, for which embodiments of the present disclosure can be used.

[25]P. Stat Comput (2006) 16: 203

In a further alternative embodiment, the method may be repeated for multiple selected regions, and a set of clusters identified at different selected regions of the genome can be further analysed by assessing the similarity of the set of phenotypes in each cluster to the set of phenotypes in the other clusters across the set of clusters. Conducting such an analysis can provide high-powered insights into shared biology. For example, a subset of clusters that shows associations to a disease or condition of interest across multiple selected regions can be further analysed to look for both shared and distinct pathogenic mechanisms. The result of this genome-wide cluster analysis can be exploited to further improve the statistical power of the embodiment outlined above, by using the frequency at which certain pluralities of phenotypes co-occur in clusters as a prior with which these phenotypes are proposed to cluster. This can be achieved in various ways. One way is to use the Ising model; define a "cluster membership" vector $m_r$ for a selected region r and a given cluster C, coordinates of which are 1 when a study is part of non-null cluster C, and 0 if it is part of the null cluster or any other cluster in selected region r, and GAS co-clustering can then be modelled by including a term $$L(k) = \frac{1}{Z(J, h)} \exp\left[\sum_{j \neq i} J_{ij} m_{ri} m_{rj} + \sum_i h_i m_{ri}\right]$$

in the model, where J and h are modeling parameters, and Z(J, h) is a normalization constant, the value of which is difficult to compute but not required for the update equations. This term replaces the factors p and 1−p for membership of the null cluster and non-null clusters respectively, because of the presence of the linear term $\Sigma_i h_i m_{ri}$ which models the marginal probability that a GAS participates in any cluster in selected region r. Alternatively since the linear term $\Sigma_i h_i m_{ri}$ models the marginal probability that study i is involved in a cluster, this term could be left out and the factors p and 1−p be used as in the standard embodiment.

The modeling parameters J and h are found by optimising the total clustering likelihood Z(J,h) over the inferred cluster membership vectors m.

In another further embodiment the meta analysis function, $meta_{is}$, of variant i within cluster s that is used when calculating the characteristics of a cluster does not assume studies to be independent, but takes account of correlations between studies. This embodiment can both account for the cryptic correlation in effect size estimates between GAS (or phenotypes), and make specific assumptions about the size and correlation in true effects between studies. Cryptic correlation between studies can arise due to association GAS of different phenotypes being performed on an overlapping set of individuals. A natural way of assessing the evidence for association in this setting involves modelling both the true effects, and the sampling error, with multivariate normal distributions so as to obtain a multivariate marginal likelihood (see for example Supplementary Methods of Band et al.)[26] of the form $$MVN(\hat{\beta};0,\Sigma+V).$$

[26]PLoS Genet 9(5): e1003509

The MVN function is a multivariate normal density, evaluated at $\hat{\beta}_{is}$, the vector of observed effect size estimates, with mean vector of Os, and variance-covariance determined by $V=(SE_{is})R_{cryptic}(SE_{is})^T$, and $\Sigma=\sigma R_{true}$. $R_{true}$ is the assumed correlation in true effects, which might be an identity matrix when assuming that the size and direction of effects are uncorrelated. $R_{cryptic}$ is the assumed correlation in uncertainty in the beta estimates between GAS, and can be estimated from the empirical correlation in beta estimates between each pair of studies (ideally, but not necessarily, genome-wide). As above, σ, is the variance in the prior distribution on the true effect, and σ=0 under the null hypothesis of no association. The meta-analysis of the evidence for association at a variant is then a Bayes Factor based on the ratio of the marginal likelihoods $$meta_{is} = \frac{MVN(\hat{\beta}; 0, \Sigma + V)}{MVN(\hat{\beta}; 0, V)}.$$

Note that when both Σ and V are diagonal then studies are assumed to be independent and the example embodiment of $meta_{is}$, is recovered. A computationally efficient approximation involves clustering under the independence assumption but then performing the multivariate normal meta-analysis as a final step to make cluster assignments. An alternative computationally efficient embodiment involves updating the matrices $\Sigma^{-1}$ and $(V+\Sigma)^{-1}$ and their determinants, which are required for the calculation of $meta_{is}$, using the Sherman-Morrison formula and the Matrix Determinant Lemma.

The invention claimed is:

1. A computer-implemented method of analysing genetic data about an organism, comprising:
    accessing a plurality of genome-wide association studies;
    deriving, using the plurality of genome-wide association studies, at least 50 input units, wherein:
        each input unit is a data structure derived from a genome-wide association study of the plurality of genome-wide association studies that provides summary statistic data including an inferred effect size of each of a plurality of genetic variants along a genome of the organism on a phenotype corresponding to the input unit and a standard error of the inferred effect size, and
    the deriving comprises:
        completing each genome-wide association study having missing data about an association between one or more genetic variants and the phenotype corresponding to the input unit by modeling the association between the one or more genetic variants and the phenotype corresponding to the input unit, and
    determining a set of characteristics for each input unit based on the summary statistic data associated with the genome-wide association study the set of characteristics comprising probability metrics which quantify evidence for each of the plurality of genetic variants being causal for the phenotype corresponding to the input unit;
    selecting a region or regions of the genome of the organism;
    for each of the selected region or regions, assigning each of the input units to one or more of a plurality of clusters, the assigning being an iterative process for exploring a space of possible assignment using a Markov Chain Monte Carlo (MCMC) algorithm designed to effectively explore an exponentially large space of study assignments, the iterative process comprising:
        determining a degree of similarity between i) the set of characteristics of the input unit, and ii) a set of characteristics of each of the plurality of clusters, wherein the set of characteristics of each cluster is either pre-determined or calculated by combining the sets of characteristics of input units already assigned to the cluster, and
        either a) assigning the input unit to one or more existing clusters of the plurality of clusters with a probability dependent on the corresponding degree of similarity, or
        b) creating a new cluster in the plurality of clusters and assigning the input unit to the new cluster with a probability dependent on the set of characteristics of the input unit and the sets of characteristics of the existing clusters of the plurality of clusters;
    identifying that the phenotypes corresponding to the input units assigned to the same cluster share underlying biological mechanisms; and
    displaying, for each of the selected region or regions, an analysis across all input units using a computer-based interface that summarizes a membership of each of the clusters and the assignment of each of the genetic variants to each cluster based on the assigning and the identifying.

2. The method of claim 1, wherein the assignment of each of the input units to one or more of the plurality of clusters is based on assessing said assignment using a Bayesian probabilistic model.

3. The method of claim 1, wherein the assignment of each of the input units to one or more of the plurality of clusters is based on an analysis of a path taken by the Markov chain.

4. The method of claim 1, wherein one step of the Markov chain Monte Carlo algorithm comprises the assignment of one of the input units to one or more of the plurality of clusters with a probability dependent on the degree of similarity between the set of characteristics of the input unit and the set of characteristics of the cluster.

5. The method of claim 1, wherein the plurality of clusters comprises a null cluster.

6. The method of claim 1, wherein the assignment of each of the input units to one or more of the plurality of clusters further comprises using a prior distribution on a number and/or size of clusters.

7. The method of claim 6, wherein the prior distribution on the number and/or size of clusters follows a Chinese Restaurant Process.

8. The method of claim 1, wherein:
the sets of characteristics of the input units are determined by calculating Bayes factors of each of the plurality of genetic variants in the input unit;
the set of characteristics of each of the plurality of clusters is calculated by combining the sets of characteristics of input units already assigned to the cluster; and
combining the sets of characteristics of input units already assigned to the cluster comprises calculating a product of the Bayes factors of the input units assigned to the cluster.

9. The method of claim 1, wherein calculating the set of characteristics of a cluster comprises using a prior distribution of the probabilities of each of the plurality of genetic variants being causal.

10. The method of claim 9, wherein the prior distribution of the probabilities incorporates pre-existing information about variation in functionality relevant to causality over the genetic variants.

11. The method of claim 1, wherein calculating the set of characteristics of a cluster further comprises taking account of correlations or other known relationships between the genome-wide association studies used to derive the input units.

12. The method of claim 1, wherein the assignment of each of the input units to one or more of the plurality of clusters further comprises using a prior distribution on pairs or larger collections of input units being assigned to the same cluster.

13. The method of claim 1, further comprising outputting a probability distribution over aspects of cluster membership, and characterising certainty around cluster assignment.

14. The method of claim 1, further comprising iteratively repeating the assignment of the input units to one or more of the plurality of clusters until a predetermined convergence threshold is reached or a predetermined number of iterations has been performed.

15. The method of claim 1, further comprising, for each of one or more of the plurality of clusters, identifying one or more lead genetic variants from the plurality of genetic variants that are causal for one or more phenotypes corresponding to the cluster.

16. The method of claim 15, further comprising:
calculating a size of an effect of the one or more lead genetic variants on a target phenotype;
determining a genotype of an individual organism with respect to each of the one or more lead genetic variants; and
calculating a contribution of the genotype of the individual organism to the target phenotype of the individual organism on the basis of the sizes of the effect of the one or more lead genetic variants on the target phenotype.

17. The method of claim 16, further comprising combining the contribution of the genotype of the individual organism to the target phenotype with other clinical and/or genetic data about the individual organism to improve a determination of the target phenotype of the individual organism.

18. The method of claim 15, wherein two or more lead genetic variants are identified for each of one or more clusters, and identifying the two or more lead genetic variants comprises calculating a matrix of correlations between genetic variants.

19. The method of claim 15, wherein two or more lead genetic variants are identified for each of one or more clusters, and the identifying of two or more lead genetic variants comprises:
calculating a set of characteristics of the cluster quantifying the probability of each of the genetic variants being causal for the cluster;
determining a first lead genetic variant for the cluster on the basis of the set of characteristics of the cluster;
updating the set of characteristics of the cluster to account for the effect of the first lead genetic variant; and
determining a second lead genetic variant for the cluster on the basis of the updated set of characteristics.

20. The method of claim 1, wherein the plurality of genetic variants are chosen from genetic variants in the selected region of the genome, and the selected region comprises a predetermined number of base pairs and includes a gene of interest.

21. The method of claim 20, wherein the selected region is chosen by minimising the correlation between genetic variants in the selected region, and genetic variants in one or more other regions of the genome.

22. The method of claim 20, wherein the method is performed for each of a plurality of selected regions of the genome, thereby providing a plurality of sets of clusters containing assigned input units, each set of clusters corresponding to a different one of the selected regions, the method further comprising associating a first subset of one or more clusters from a first set with a second subset of one or more clusters from each of one or more other sets by assessing a similarity between phenotypes corresponding to input units in the first subset of clusters with phenotypes corresponding to input units in the one or more second subsets of clusters.

23. The method of claim 22, further comprising identifying a group of phenotypes corresponding to input units which are assigned to the same cluster across the plurality of sets with a frequency above a predetermined frequency threshold.

24. The method of claim 1, wherein one or more of the input units further comprise additional information about the association between one or more genetic variants in the selected region or regions of the genome and the phenotype corresponding to the input unit, and the additional information is obtained by modelling the association between the one or more genetic variants and the phenotype corresponding to the input unit.

25. The method of claim 1, wherein the phenotypes corresponding to the input units include one or more of: a level of expression of a gene; regulation of expression of a gene; epigenetic characteristics; a level of abundance of a protein or peptide; the function and/or molecular structure of a protein or peptide; a quantity of a molecule in the organism; characteristics of biochemical and metabolic processes; cellular properties, including morphology and function; tissue properties, including morphology and function; organ and organ system properties, including morphology and function; any response to an external stimulus or stimuli; any response to exposure to a substance or pathogen; behavioural and lifestyle characteristics; reproductive and life course characteristics and function; the onset, trajectory, and prognosis of a disease or condition; a measurable anatomical characteristic; a measurable physiological or functional characteristic; and measurable psychological or cognitive characteristics.

26. The method of claim 1, wherein the identification of phenotypes that share underlying biological mechanisms comprises identification of one or more of the following combinations of phenotypes:
   i) an occurrence of a disease or condition and one or more of a level of expression of a gene, a level of expression of a protein or peptide, a quantity of a biological molecule in the organism;
   ii) a measurable characteristic of the organism and one or more of a level of expression of a gene, a level of expression of a protein or peptide, a quantity of a biological molecule in the organism;
   iii) an occurrence of a disease or condition and a measurable characteristic of the organism;
   iv) a response to an input of a substance to the organism and one or more of an occurrence of a disease or condition, a measurable characteristic of the organism, a quantity of a biological molecule in the organism; and
   v) a level of expression of a gene and one or more of a level of expression of a different gene, a level of expression of a protein or peptide, a quantity of a biological molecule in the organism.

27. The method of claim 1, wherein the method comprises, on the basis of the identification of phenotypes that share underlying biological mechanisms, one or more of:
   (i) determining clinical support strategies for the organism;
   (ii) determining a probability of the organism developing a disease or condition;
   (iii) stratifying the organism in a clinical or pre-clinical trial;
   (iv) identifying a biological pathway in the organism; or
   (v) where the phenotypes corresponding to the input units include a response of the organism to input of one or more new or existing drugs, one or more of:
      (a) determining the mechanism of action of the one or more drugs;
      (b) determining the clinical and/or adverse response of the organism to the one or more drugs;
      (c) determining biomarkers of the one or more drugs; or
      (d) determining to which subsets of patients the drug should or should not be given to achieve particular clinical or safety outcomes.

28. The method of claim 1, wherein the phenotypes corresponding to the input units include the response of an organism to input of two or more new or existing drugs, and the method comprises, on the basis of the identification of phenotypes directly or indirectly causally associated with each other, one or more of:
   (i) determining interactions between the two or more drugs; or
   (ii) determining the effect on the organism of interactions between the two or more drugs.

29. The method of claim 1, wherein further analysis of the sets of clusters obtained when the method is applied to different regions of the genome is used to identify biological features, properties, or mechanisms, which are shared between more than one of the sets of clusters in order to identify any of:
   (i) intermediate molecular, cellular, or other phenotypes which occur on the path to a particular disease outcome or set of outcomes;
   (ii) the use of phenotypes identified in (i) above as therapeutic targets;
   (iii) the use of phenotypes identified in (i) or (ii) above as readouts in assays in drug development or as biomarkers in drug development;
   (iv) the use of phenotypes identified in any of (i)-(iii) above to stratify patients in clinical trials; or
   (v) the use of phenotypes identified in any of (i)-(iv) above to determine a plurality of subsets of patients to whom particular therapeutics or treatments or combinations of therapeutics or treatments should or should not be given in order to aim to achieve particular outcomes.

30. A computer-implemented method of analysing genetic data about an organism to provide treatment or prevention of a disease or condition, the method comprising:
   accessing a plurality of genome-wide association studies;
   receiving input data comprising a plurality of deriving, using the plurality of genome-wide association studies, at least 50 input units, wherein:
      each input unit is a data structure derived from a genome-wide association study of the plurality of genome-wide association studies that provides summary statistic data including an inferred effect size of each of a plurality of genetic variants along a genome of the organism on a phenotype corresponding to the input unit and a standard error of the inferred effect size, and
      the deriving comprises:
         completing each genome-wide association study having missing data about an association between one or more genetic variants and the phenotype corresponding to the input unit by modeling the association between the one or more genetic variants and the phenotype corresponding to the input unit, and
         determining a set of characteristics for each input unit based on the summary statistic data associated with the genome-wide association study, the set of characteristics comprising probability metrics which quantify evidence for each of the plurality of genetic variants being causal for the phenotype corresponding to the input unit;
   selecting a region or regions of the genome of the organism;
   for each of the selected region or regions, assigning each of the input units to one or more of a plurality of clusters, the assigning being an iterative process for exploring a space of possible assignment using a Markov Chain Monte Carlo (MCMC) algorithm designed to effectively explore an exponentially large space of study assignments, the iterative process comprising:
      determining a degree of similarity between i) the set of characteristics of the input unit, and ii) a set of characteristics of each of the plurality of clusters, wherein the set of characteristics of each cluster is either pre-determined or calculated by combining the sets of characteristics of input units already assigned to the cluster; and
      either a) assigning the input unit to one or more existing clusters of the plurality of clusters with a probability dependent on the corresponding degree of similarity; or
      b) creating a new cluster in the plurality of clusters and assigning the input unit to the new cluster with a probability dependent on the set of characteristics of the input unit and the sets of characteristics of the existing clusters of the plurality of clusters;

identifying that the phenotypes corresponding to input units assigned to the same cluster share underlying biological mechanisms; and on the basis of the identification of phenotypes that share underlying biological mechanisms, one or more of:

(i) outputting clinical support strategies for the organism;

(ii) determining outputting a probability of the organism developing a disease or condition; and (iii) where the phenotypes corresponding to the input units include the response of the organism to input of one or more new or existing drugs, outputting the clinical and/or adverse response of the organism to the one or more drugs.

\* \* \* \* \*